United States Patent
Du et al.

(10) Patent No.: US 7,220,539 B1
(45) Date of Patent: May 22, 2007

(54) PROTEIN KINASE B/AKT MODULATORS AND METHODS FOR THE USE THEREOF

(75) Inventors: Keyong Du, San Diego, CA (US); Stephan Herzig, Del Mar, CA (US); Marc Montminy, San Diego, CA (US)

(73) Assignee: The Salk Institute for Biological Studies, La Jolla, CA (US)

( * ) Notice: Subject to any disclaimer, the term of this patent is extended or adjusted under 35 U.S.C. 154(b) by 373 days.

(21) Appl. No.: 10/462,072

(22) Filed: Jun. 12, 2003

Related U.S. Application Data

(60) Provisional application No. 60/388,508, filed on Jun. 12, 2002.

(51) Int. Cl.
  C12Q 1/00 (2006.01)
  C12N 9/12 (2006.01)
  C12N 1/20 (2006.01)
  C07K 1/00 (2006.01)
  C07H 21/04 (2006.01)

(52) U.S. Cl. .......................... 435/4; 435/7.1; 435/183; 435/194; 435/252.3; 435/320.1; 530/350; 536/23.1; 536/23.2

(58) Field of Classification Search ............... 435/4, 435/7.1, 183, 194, 252.3, 320.1; 530/350; 536/23.1, 23.2
See application file for complete search history.

(56) References Cited

OTHER PUBLICATIONS

Iynedijan. Biochem. J. (2005) 386, 113-118.*
Laine et al. Mol Cell. Aug. 2000;6(2):395-407.*
Kandel et al. Exp Cell Res. Nov. 25, 1999;253(1):210-29.*
Altschul et al., "Basic alignment search tool." *J. Mol. Biol.* 215:403-410 1990.
Altschul et al., "Gapped BLAST and PSI-BLAST: a new generation of protein database search programs." *Nucl. Acids Res.* 25:3389-3402 1977.
Aman et al., "The inositol phosphatase SHIP inhibits Akt/PKB activation in B cells." *J. Biol. Chem.* 273:33922-33928, 1998.
Backman et al., "Deletion of *Pten* in mouse brain causes seizures, ataxia and defects in soma size resembling Lhermitte-Duclos disease." *Nat. Genet.* 29:396-403, 2001.
Becker et al., "Use of recombinant adenovirus for metabolic engineering of mammalian cells." *Meth. Cell. Biol.* 43A:161-189, 1994.
Brady et al., "The Activation of Glycogen Synthase by Insulin Switches from Kinase Inhibition to Phosphatase Activation during Adipogenesis in 3T3-L1 Cells." *J. Biol. Chem* 273:14063-14066, 1998.
Chen et al., "Growth retardation and increased apoptosis in mice with homozygous disruption of the akt1 gene." *Genes Dev.* 15:2203-2208, 2001.
Cho et al., "Akt1/PKBα Is Required for Normal Growth but Dispensable for Maintenance for Glucose Homeostasis in Mice." *J. Biol. Chem.* 276:38349-38352, 2001.

Cho et al., "Insulin Resistance and a Diabetis Mellitus-Like Syndrome in Mice Lacking the Protein Kinase Akt2 (PKBβ)." *Science* 292:1728-1731, 2001.
Delcommenne et al., "Phosphoinositide-3-OH kinase-dependent regulation of glycogen synthase kinase 3 and protein kinase B/ AKT by the integrin-linked kinase." *Proc. Natl. Acad. Sci.* 95:11211-11216, 1998.
Elbashir et al., <<Duplexes of 21-nucleotide RNAs mediate RNA interference in cultured mammalian cells.>> *Nature* 411:494-498, 2001.
Gonnet et al., "Exhaustive Matching of the Entire Protein Sequence Database." *Science* 256:1443-1445 1992.
Guo et al., "Phosphorylation of Serine 256 by Protein Kinase B Disrupts Transactivation by FKHR and Mediates Effects of Insulin on Insulin-like Growth Factor-binding Protein-1 Promoter Activity through a Conserved Insulin Response Sequence." *J. Biol. Chem.* 274:17184-17192, 1999.
Hajduch et al., "Constitutive Activation of Protein Kinase Bα by Membrane Targeting Promotes Glucose and System A Amino Acid Transport, Protein Synthesis, and Inactivation of Glycogen Synthase Kinase 3 and Inactivation of Glycogen Synthase Kinase 3 in L6 Muscle Cells." *Diabetes* 47:1006-1013, 1998.
Hanks and Hunter, "The eukaryotic protein kinase superfamily: kinase (catalytic) domain structure and classification." *FASEB J.* 9:576-596, 1995.
He et al., "A simplified system for generating recombinant adenoviruses." *Proc. Natl. Acad. Sci. USA* 95:2509-2514, 1998.
Henikoff & Henikoff, "Amino Acid Substitution Matrices from Protein Blocks." *Proc. Natl. Acad. Sci. USA* 89:10915 1989.
Henikoff and Henikoff, "Performance Evaluation of Amino Acid Substitution Matrices." Proteins 17:49-61 1993.
Herzig et al., "CREB regulates hepatic gluconeogenesis through the coactivator PGC-1." *Nature* 413:179-183, 2001.
Karlin & Altschul, "Applications and Statistics for Multiple High-Scoring Segments in Molecular Sequences." *Proc. Natl. Acad. Sci. USA* 90:5873 1993.
Kops et al., "Direct control of the Forkhead transcription factor AFX by protein kinase B." *Nature* 398:630-634, 1999.
Liu et al., "SHIP is a negative regulator of growth factor receptor-mediated PKB/ Akt activation and myeloid cell survival." *Genes Dev.* 13:786-791, 1999.

(Continued)

*Primary Examiner*—Tekchand Saidha
*Assistant Examiner*—Christian L. Fronda
(74) *Attorney, Agent, or Firm*—Foley & Lardner LLP; Stephen E. Reiter

(57) ABSTRACT

The present invention describes modulator of protein kinase B (PKB)/Akt proteins, exemplified by the Tribbles (TRB) family. An exemplary member of the TRB family, TRB-3, binds to Akt and inhibits its catalytic activity, in turn causing altered regulation of glucose metabolism pathways. TRB-3 expression is strongly induced in the fasting state, and upregulated in mouse models of type II, causing disruptions in insulin signaling. Accordingly, the present invention further provides compositions and methods for disrupting the interaction between such a modulator and PKB/Akt protein kinases. Also provided are methods of determining if a subject has a predisposition to impaired glucose regulation and methods for treating diabetes mellitus using invention compositions.

15 Claims, 9 Drawing Sheets

OTHER PUBLICATIONS

Maira et al., "Carboxyl-Terminal Modulator Protein (CTMP), a Negative Regulator of PKB/ Akt and v-Akt at the Plasma Membrane." *Science* 294:374-380, 2001.

Mata et al., "Tribbles Coordinates Mitosis and Morphogenesis in *Drosophila* by Regulating String/CDC25 Proteolysis." *Cell* 101:511-522, 2000.

Mayumi-Matsuda, "Identification of a Novel Kinase-like Gene Induced during Neuronal Cell Death." *Biochem. Biophys. Res. Commun.* 258:260-264, 1999.

Meier et al., "Inactivation and dephosphorylation of protein kinase Bα (PKBα) promoted by hyperosmotic stress." *EMBO J.* 17:7294-7303, 1998.

Michael et al., "The Phosphorylation Status of a Cyclic AMP-Responsive Activator Is Modulated via a Chromatin-Dependent Mechanism."*Mol. Cell. Biol.* 20:1596-1603, 2000.

Mitsuuchi et al., "Translocation and Activation of AKT2 in Response to Stimulation by Isulin." *J. Cell. Biochem.* 70:433-443, 1998.

Nakae et al., "Insulin Stimulates Phosphorylation of the Forkhead Transcription Factor FKHR on Serine 253 through a Wortmannin-sensitive Pathway." *J. Biol. Chem.* 274:15982-15985, 1999.

Nakajima et al., "RNA Helicase A Mediates Association of CBP with RNA Polymerase II." *Cell* 90:1107-1112, 1997.

Paez-Espinosa et al., "Insulin-induced tyrosine phosphorylation of Shc in liver, muscle and adipose tissue of insulin resistant rats." *Mol. Cell. Endocrinol.* 156:121-129, 1999;.

Ramaswamy et al., "Regulation of $G_1$ Progression by the PTEN Tumor Suppressor Protein Is Linked to Inhibition of the Phosphatidylinositol 3-Kinase/ Akt Pathway." *Proc. Natl. Acad. Sci. USA* 96:2110-2115, 1999.

Rao, "Adaptations in Glucose Homeostasis During Chronic Nutritional Deprivation in Rats: Hepatic Resistance to Both Insulin and Glucagon." *Metabolism* 44:817-824, 1995.

Rorth et al., "The Level of C/EBP Protein Is Critical for Cell Migration during *Drosophila* Oogenesis and Is Tightly Controlled by Regulated Degradation." *Mol. Cell.* 6:23-30, 2000.

Seher and Leptin, "Tribbles, a cell-cycle brake that coordinates proliferation and morphogenesis during *Drosophila* gastrulation." *Curr. Biol.* 10:623-629, 2000.

van Weeren, "Essential Role for Protein Kinase B (PKB) in Insulin-induced Glycogen Synthase Kinase 3 Inactivation. Charcterization of Dominant-Negative Mutant of PKB." *J. Biol. Chem.* 273:13150-13156, 1998.

Wilkin et al., "Characterization of a Phosphoprotein whose mRNA is regulated by the mitogenic pathways in dog thyroid cells." *Eur. J. Biochem.* 248:660-668, 1997.

Wilkin et al., "Identification and Characterization of Novel Genes Modulated in the Thyroid of Dogs Treated with Methimazole and Propylthiouracil." *J. Biol. Chem.* 271:28451-28457, 1996.

Williams et al., "The role 3-phospoinositide-dependent protein kinase 1 in activating AGC kinases defined in embryonic stem cells." *Curr. Biol.* 10:439-448, 2000.

Yeagley et al., "Characterization of Elements Mediating Regulation of Phosphoenolpyruvate Carboxykinase Gene Transcription by Protein Kinase A and Insulin. Identification of a distinct complex formed in cells that mediate insulin inhibition." *J. Biol. Chem.* 275:17814-17820, 2000.

Yoon et al., "Control of hepatic gluconeogenesis through the transcriptional coactivator PGC-1." *Nature* 413:131-138, 2001.

\* cited by examiner

```
           20                  40                            60                  80
hum 1 MRATPLAAPAGSLSRKKRLELDDNLDTERPVQKRARSGPQPRLPPCLLPLSPPTAPDRATAVATASRLGPYVLLEPEEGG
rat 1 MRATSLAASADVPCRKKPLEFDDNIDVECPVLKRVRDEPEP==GP==TP=SLPPASDLSPAVAPATRLGPYILLEREQGN
mou 1 MRATPLAASADVSCRKKPLEFDDNIDAKCPVLKRVRDEPEPGPLPSLLPPSPPPASDLSPAVAPATRLGPYILLEREQGS
C5FW                                                                IGKYLLLEPLEGD
C8FW
Tribbles 100                 120                 140                 160
RAYQALHCPTGTEYTCKVYPVQEALAVLEPYARLPPHKHVARPTEVLAGTQLLYAFFTRTHGDMHSLVRSRHRIPEPEAA
CTYRALHCPTGTEYTCKVYPASEAQAVLAPYARLPTHQHVARPTEVLLGSQLLYTFFTKTHGDLHSLVRSRRGIPEPEAA
                                        VLGETKAYVFFEKSFGDMHSYVRSRKRLREEEAA
                                        TGVYENLHTYIRHAKRLCETEAR 180                 200                 220                 240
VLFRQMATALAHCHQHGLVLRDLKLCRFVFADRERKKLVLENLEDSCVLTGPDDSLWDKHACPAYVGPEILSSRASYSGK
ALFRQMASAVAHCHKHGLILRDLKLRRFVFSNCERTKLVLENLEDACVMTGPDDSLWDKHACPAYVGPEILSSRPSYSGR
GLFRQMASAVAHCHKHGLVLRDLKLRRFVFSNCERTKLVLENLEDACVMTGSDDSLWDKHACPAYVGPEILSSRPSYSGK
RLFYQIASAVAHCHDGGLVLRDLKLRKFIFKDEERTRVKLESLEDAYILRGDDDSLSDKHGCPAYVSPEILNTSGSYSGK
RLFKQIVSAVAHCHQSAIVLGDLKLRKFVFSTEERTQLRLESLEDTHIMKGEDDALSDKHGCPAYVSPEILNTTGTYSGK
AIFHQICQTVQVCHRNGIILRDLKLRRFYFIDEARTKLQYESLEGSMILDGEDDTLSDKIGCPLYTAPELLCPQQTYKGK
              260                 280                 300                 30
AADVWSLGVALFTMLAGHYPFQDSEPVLLFGKIRRGAYALPAGLSAPARCLVRCLLRREPAERLTATGILLHPWLRQDPM
AADVWSLGVALFTMLAGRYPFQDSEPALLFGKIRRGTFALPEGLSASARCLIRCLLRREPSERLVALGILLHPWLREDCS
AADVWSLGVALFTMLAGRYPFHDSEPVLLFGKIRRGTFALPEGLSAPARCLIRCLLRKEPSERLVALGILLHPWLREDHG
AADVWSLGVMLYTMLVGRYPFHDIEPSSLFSKIRRGQFNIPETLSPKAKCLIRSILRREPSERLTSQEILDHPWFSTDFS
AADVWSLGVMLYTLLVGRYPFHDSDPSALFSKIRRGQFCIPEHISPKARCLIRSLLRREPSERLTAPEILLHPWF ESVL
PADMWSLGVILYTMLVGQYPFYEKANCNLITVIRHGNVQIPLTLSKSVRWLLLSLLRKDYTERMTASHIFLTPWLRE   (SEQ ID NO:6)
              340
PLAPTRSHLWEAAQVVPDGLGLDEAREEEGDREVVLYG 358  (SEQ ID NO:1)
QVSPPRSDRREMDQVVPDGPQLEEA=EE=G==EVGLYG 349  (SEQ ID NO:2)
RVSPPQSDRREMDQVVPDGPQLEEA=EE=G= EVGLYG 354  (SEQ ID NO:3)
VSNSGYGAKEVSDQLVPD  (SEQ ID NO:4)
EPGYIDSEIGTSDQIVPE  (SEQ ID NO:5)
```

FIGURE 1

A.
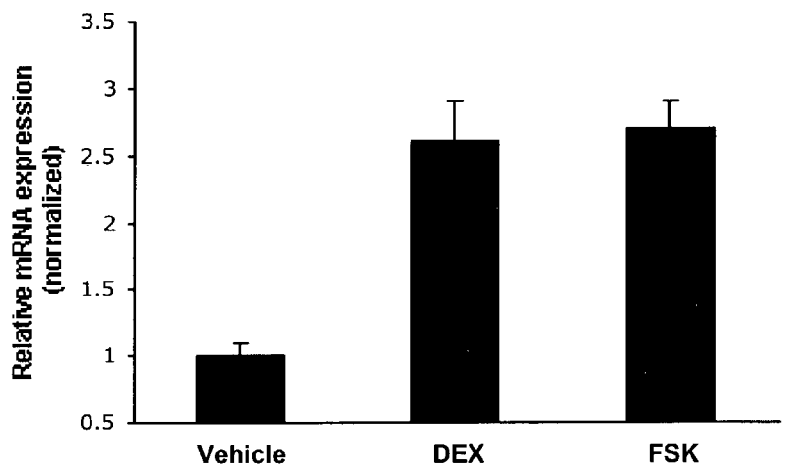
B.
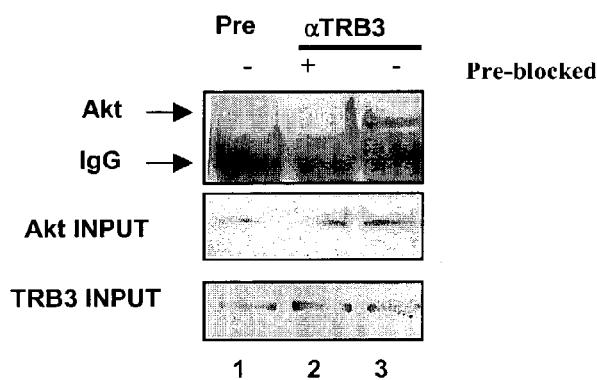
C.
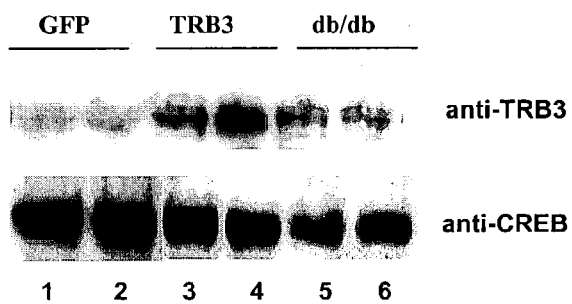
FIGURE 9

SEQUENCE LISTING

```
<160> NUMBER OF SEQ ID NOS: 15

<210> SEQ ID NO 1
<211> LENGTH: 358
<212> TYPE: PRT
<213> ORGANISM: Homo sapiens

<400> SEQUENCE: 1

Met Arg Ala Thr Pro Leu Ala Ala Pro Ala Gly Ser Leu Ser Arg Lys
  1               5                  10                  15

Lys Arg Leu Glu Leu Asp Asp Asn Leu Asp Thr Glu Arg Pro Val Gln
                 20                  25                  30

Lys Arg Ala Arg Ser Gly Pro Gln Pro Arg Leu Pro Pro Cys Leu Leu
             35                  40                  45

Pro Leu Ser Pro Pro Thr Ala Pro Asp Arg Ala Thr Ala Val Ala Thr
         50                  55                  60

Ala Ser Arg Leu Gly Pro Tyr Val Leu Leu Glu Pro Glu Gly Gly
 65                  70                  75                  80

Arg Ala Tyr Gln Ala Leu His Cys Pro Thr Gly Thr Glu Tyr Thr Cys
                 85                  90                  95

Lys Val Tyr Pro Val Gln Glu Ala Leu Ala Val Leu Glu Pro Tyr Ala
                100                 105                 110

Arg Leu Pro Pro His Lys His Val Ala Arg Pro Thr Glu Val Leu Ala
            115                 120                 125

Gly Thr Gln Leu Leu Tyr Ala Phe Phe Thr Arg Thr His Gly Asp Met
        130                 135                 140

His Ser Leu Val Arg Ser Arg His Arg Ile Pro Glu Pro Glu Ala Ala
145                 150                 155                 160

Val Leu Phe Arg Gln Met Ala Thr Ala Leu Ala His Cys His Gln His
                165                 170                 175

Gly Leu Val Leu Arg Asp Leu Lys Leu Cys Arg Phe Val Phe Ala Asp
            180                 185                 190

Arg Glu Arg Lys Lys Leu Val Leu Glu Asn Leu Glu Asp Ser Cys Val
        195                 200                 205

Leu Thr Gly Pro Asp Asp Ser Leu Trp Asp Lys His Ala Cys Pro Ala
    210                 215                 220

Tyr Val Gly Pro Glu Ile Leu Ser Ser Arg Ala Ser Tyr Ser Gly Lys
225                 230                 235                 240

Ala Ala Asp Val Trp Ser Leu Gly Val Ala Leu Phe Thr Met Leu Ala
                245                 250                 255

Gly His Tyr Pro Phe Gln Asp Ser Glu Pro Val Leu Leu Phe Gly Lys
            260                 265                 270

Ile Arg Arg Gly Ala Tyr Ala Leu Pro Ala Gly Leu Ser Ala Pro Ala
        275                 280                 285

Arg Cys Leu Val Arg Cys Leu Leu Arg Arg Glu Pro Ala Glu Arg Leu
    290                 295                 300
```

```
Thr Ala Thr Gly Ile Leu Leu His Pro Trp Leu Arg Gln Asp Pro Met
305                 310                 315                 320

Pro Leu Ala Pro Thr Arg Ser His Leu Trp Glu Ala Ala Gln Val Val
                325                 330                 335

Pro Asp Gly Leu Gly Leu Asp Glu Ala Arg Glu Glu Glu Gly Asp Arg
            340                 345                 350

Glu Val Val Leu Tyr Gly
            355

<210> SEQ ID NO 2
<211> LENGTH: 349
<212> TYPE: PRT
<213> ORGANISM: Rattus sp.

<400> SEQUENCE: 2

Met Arg Ala Thr Ser Leu Ala Ala Ser Ala Asp Val Pro Cys Arg Lys
  1               5                  10                  15

Lys Pro Leu Glu Phe Asp Asp Asn Ile Asp Val Glu Cys Pro Val Leu
                 20                  25                  30

Lys Arg Val Arg Asp Glu Pro Glu Pro Gly Pro Thr Pro Ser Leu Pro
             35                  40                  45

Pro Ala Ser Asp Leu Ser Pro Val Ala Pro Ala Thr Arg Leu Gly
         50                  55                  60

Pro Tyr Ile Leu Leu Glu Arg Glu Gln Gly Asn Cys Thr Tyr Arg Ala
 65                  70                  75                  80

Leu His Cys Pro Thr Gly Thr Glu Tyr Thr Cys Lys Val Tyr Pro Ala
                 85                  90                  95

Ser Glu Ala Gln Ala Val Leu Ala Pro Tyr Ala Arg Leu Pro Thr His
                100                 105                 110

Gln His Val Ala Arg Pro Thr Glu Val Leu Leu Gly Ser Gln Leu Leu
            115                 120                 125

Tyr Thr Phe Phe Thr Lys Thr His Gly Asp Leu His Ser Leu Val Arg
130                 135                 140

Ser Arg Arg Gly Ile Pro Glu Pro Glu Ala Ala Ala Leu Phe Arg Gln
145                 150                 155                 160

Met Ala Ser Ala Val Ala His Cys His Lys His Gly Leu Ile Leu Arg
                165                 170                 175

Asp Leu Lys Leu Arg Arg Phe Val Phe Ser Asn Cys Glu Arg Thr Lys
            180                 185                 190

Leu Val Leu Glu Asn Leu Glu Asp Ala Cys Val Met Thr Gly Pro Asp
        195                 200                 205

Asp Ser Leu Trp Asp Lys His Ala Cys Pro Ala Tyr Val Gly Pro Glu
210                 215                 220

Ile Leu Ser Ser Arg Pro Ser Tyr Ser Gly Arg Ala Ala Asp Val Trp
225                 230                 235                 240

Ser Leu Gly Val Ala Leu Phe Thr Met Leu Ala Gly Arg Tyr Pro Phe
                245                 250                 255

Gln Asp Ser Glu Pro Ala Leu Leu Phe Gly Lys Ile Arg Arg Gly Thr
            260                 265                 270

Phe Ala Leu Pro Glu Gly Leu Ser Ala Ser Ala Arg Cys Leu Ile Arg
        275                 280                 285

Cys Leu Leu Arg Arg Glu Pro Ser Glu Arg Leu Val Ala Leu Gly Ile
290                 295                 300

Leu Leu His Pro Trp Leu Arg Glu Asp Cys Ser Gln Val Ser Pro Pro
305                 310                 315                 320
```

```
Arg Ser Asp Arg Arg Glu Met Asp Gln Val Val Pro Asp Gly Pro Gln
            325                 330                 335

Leu Glu Glu Ala Glu Glu Gly Glu Val Gly Leu Tyr Gly
            340                 345

<210> SEQ ID NO 3
<211> LENGTH: 308
<212> TYPE: PRT
<213> ORGANISM: Mus musculus

<400> SEQUENCE: 3

Met Arg Ala Thr Pro Leu Ala Ala Ser Ala Asp Val Ser Cys Arg Lys
  1               5                  10                  15

Lys Pro Leu Glu Phe Asp Asp Asn Ile Asp Ala Lys Cys Pro Val Leu
             20                  25                  30

Lys Arg Val Arg Asp Glu Pro Glu Pro Gly Pro Leu Pro Ser Leu Leu
         35                  40                  45

Pro Pro Ser Pro Pro Ala Ser Asp Leu Ser Pro Ala Val Ala Pro
     50                  55                  60

Ala Thr Arg Leu Gly Pro Tyr Ile Leu Leu Glu Arg Glu Gln Gly Ser
 65                  70                  75                  80

Val Leu Gly Glu Thr Lys Ala Tyr Val Phe Phe Glu Lys Ser Phe Gly
                 85                  90                  95

Asp Met His Ser Tyr Val Arg Ser Arg Lys Arg Leu Arg Glu Glu Glu
            100                 105                 110

Ala Ala Gly Leu Phe Arg Gln Met Ala Ser Ala Val Ala His Cys His
            115                 120                 125

Lys His Gly Leu Val Leu Arg Asp Leu Lys Leu Arg Arg Phe Val Phe
        130                 135                 140

Ser Asn Cys Glu Arg Thr Lys Leu Val Leu Glu Asn Leu Glu Asp Ala
145                 150                 155                 160

Cys Val Met Thr Gly Ser Asp Asp Ser Leu Trp Asp Lys His Ala Cys
                165                 170                 175

Pro Ala Tyr Val Gly Pro Glu Ile Leu Ser Ser Arg Pro Ser Tyr Ser
            180                 185                 190

Gly Lys Ala Ala Asp Val Trp Ser Leu Gly Val Ala Leu Phe Thr Met
        195                 200                 205

Leu Ala Gly Arg Tyr Pro Phe His Asp Ser Glu Pro Val Leu Leu Phe
    210                 215                 220

Gly Lys Ile Arg Arg Gly Thr Phe Ala Leu Pro Glu Gly Leu Ser Ala
225                 230                 235                 240

Pro Ala Arg Cys Leu Ile Arg Cys Leu Leu Arg Lys Glu Pro Ser Glu
                245                 250                 255

Arg Leu Val Ala Leu Gly Ile Leu Leu His Pro Trp Leu Arg Glu Asp
            260                 265                 270

His Gly Arg Val Ser Pro Pro Gln Ser Asp Arg Arg Glu Met Asp Gln
        275                 280                 285

Val Val Pro Asp Gly Pro Gln Leu Glu Glu Ala Glu Glu Gly Glu Val
    290                 295                 300

Gly Leu Tyr Gly
305

<210> SEQ ID NO 4
<211> LENGTH: 214
<212> TYPE: PRT
```

```
<213> ORGANISM: Unknown Organism
<220> FEATURE:
<223> OTHER INFORMATION: Description of Unknown Organism: Mammalian TRB
      family member

<400> SEQUENCE: 4

Ile Gly Lys Tyr Leu Leu Glu Pro Leu Glu Gly Asp Thr Gly Val
 1               5                  10                  15

Tyr Glu Asn Leu His Thr Tyr Ile Arg His Ala Lys Arg Leu Cys Glu
                20                  25                  30

Thr Glu Ala Arg Arg Leu Phe Tyr Gln Ile Ala Ser Ala Val Ala His
            35                  40                  45

Cys His Asp Gly Gly Leu Val Leu Arg Asp Leu Lys Leu Arg Lys Phe
    50                  55                  60

Ile Phe Lys Asp Glu Glu Arg Thr Arg Val Lys Leu Glu Ser Leu Glu
65                  70                  75                  80

Asp Ala Tyr Ile Leu Arg Gly Asp Asp Ser Leu Ser Asp Lys His
                85                  90                  95

Gly Cys Pro Ala Tyr Val Ser Pro Glu Ile Leu Asn Thr Ser Gly Ser
            100                 105                 110

Tyr Ser Gly Lys Ala Ala Asp Val Trp Ser Leu Gly Val Met Leu Tyr
        115                 120                 125

Thr Met Leu Val Gly Arg Tyr Pro Phe His Asp Ile Glu Pro Ser Ser
    130                 135                 140

Leu Phe Ser Lys Ile Arg Arg Gly Gln Phe Asn Ile Pro Glu Thr Leu
145                 150                 155                 160

Ser Pro Lys Ala Lys Cys Leu Ile Arg Ser Ile Leu Arg Arg Glu Pro
                165                 170                 175

Ser Glu Arg Leu Thr Ser Gln Glu Ile Leu Asp His Pro Trp Phe Ser
            180                 185                 190

Thr Asp Phe Ser Val Ser Asn Ser Gly Tyr Gly Ala Lys Glu Val Ser
        195                 200                 205

Asp Gln Leu Val Pro Asp
    210

<210> SEQ ID NO 5
<211> LENGTH: 177
<212> TYPE: PRT
<213> ORGANISM: Unknown Organism
<220> FEATURE:
<223> OTHER INFORMATION: Description of Unknown Organism: Mammalian TRB
      family member

<400> SEQUENCE: 5

Arg Leu Phe Lys Gln Ile Val Ser Ala Val Ala His Cys His Gln Ser
 1               5                  10                  15

Ala Ile Val Leu Gly Asp Leu Lys Leu Arg Lys Phe Val Phe Ser Thr
                20                  25                  30

Glu Glu Arg Thr Gln Leu Arg Leu Glu Ser Leu Glu Asp Thr His Ile
            35                  40                  45

Met Lys Gly Glu Asp Asp Ala Leu Ser Asp Lys His Gly Cys Pro Ala
    50                  55                  60

Tyr Val Ser Pro Glu Ile Leu Asn Thr Thr Gly Thr Tyr Ser Gly Lys
65                  70                  75                  80

Ala Ala Asp Val Trp Ser Leu Gly Val Met Leu Tyr Thr Leu Leu Val
            85                  90                  95

Gly Arg Tyr Pro Phe His Asp Ser Asp Pro Ser Ala Leu Phe Ser Lys
```

```
                    100                 105                 110
Ile Arg Arg Gly Gln Phe Cys Ile Pro Glu His Ile Ser Pro Lys Ala
            115                 120                 125

Arg Cys Leu Ile Arg Ser Leu Leu Arg Arg Glu Pro Ser Glu Arg Leu
    130                 135                 140

Thr Ala Pro Glu Ile Leu Leu His Pro Trp Phe Glu Ser Val Leu Glu
145                 150                 155                 160

Pro Gly Tyr Ile Asp Ser Glu Ile Gly Thr Ser Asp Gln Ile Val Pro
                165                 170                 175

Glu

<210> SEQ ID NO 6
<211> LENGTH: 157
<212> TYPE: PRT
<213> ORGANISM: Drosophila sp.

<400> SEQUENCE: 6

Ala Ile Phe His Gln Ile Cys Gln Thr Val Gln Val Cys His Arg Asn
1               5                   10                  15

Gly Ile Ile Leu Arg Asp Leu Lys Leu Arg Arg Phe Tyr Phe Ile Asp
                20                  25                  30

Glu Ala Arg Thr Lys Leu Gln Tyr Glu Ser Leu Glu Gly Ser Met Ile
            35                  40                  45

Leu Asp Gly Glu Asp Asp Thr Leu Ser Asp Lys Ile Gly Cys Pro Leu
    50                  55                  60

Tyr Thr Ala Pro Glu Leu Leu Cys Pro Gln Gln Thr Tyr Lys Gly Lys
65                  70                  75                  80

Pro Ala Asp Met Trp Ser Leu Gly Val Ile Leu Tyr Thr Met Leu Val
                85                  90                  95

Gly Gln Tyr Pro Phe Tyr Glu Lys Ala Asn Cys Asn Leu Ile Thr Val
            100                 105                 110

Ile Arg His Gly Asn Val Gln Ile Pro Leu Thr Leu Ser Lys Ser Val
        115                 120                 125

Arg Trp Leu Leu Leu Ser Leu Leu Arg Lys Asp Tyr Thr Glu Arg Met
    130                 135                 140

Thr Ala Ser His Ile Phe Leu Thr Pro Trp Leu Arg Glu
145                 150                 155

<210> SEQ ID NO 7
<211> LENGTH: 372
<212> TYPE: PRT
<213> ORGANISM: Mus musculus

<400> SEQUENCE: 7

Met Arg Val Gly Pro Val Arg Phe Ala Leu Ser Gly Ala Ser Gln Pro
1               5                   10                  15

Arg Gly Pro Gly Leu Leu Phe Pro Ala Arg Gly Thr Pro Ala Lys
                20                  25                  30

Arg Leu Leu Asp Thr Asp Asp Ala Gly Ala Val Ala Ala Lys Cys Pro
            35                  40                  45

Arg Leu Ser Glu Cys Ser Ser Pro Asp Tyr Leu Ser Pro Gly
    50                  55                  60

Ser Pro Cys Ser Pro Gln Pro Pro Ser Thr Gln Gly Thr Gly Gly
65                  70                  75                  80

Ser Cys Val Ser Ser Pro Gly Pro Ser Arg Ile Ala Asp Tyr Leu Leu
                85                  90                  95
```

-continued

```
Leu Pro Leu Ala Glu Arg Glu His Val Ser Arg Ala Leu Cys Ile His
                100                 105                 110

Thr Gly Arg Glu Leu Arg Cys Lys Glu Phe Pro Ile Lys His Tyr Gln
            115                 120                 125

Asp Lys Ile Arg Pro Tyr Ile Gln Leu Pro Ser His Ser Asn Ile Thr
        130                 135                 140

Gly Ile Val Glu Val Leu Leu Gly Glu Ser Lys Ala Tyr Val Phe Phe
145                 150                 155                 160

Glu Lys Asp Phe Gly Asp Met His Ser Tyr Val Arg Ser Arg Lys Arg
                165                 170                 175

Leu Arg Glu Glu Glu Ala Ala Arg Leu Phe Lys Gln Ile Val Ser Ala
            180                 185                 190

Val Ala His Cys His Gln Ser Ala Ile Val Leu Gly Asp Leu Lys Leu
        195                 200                 205

Arg Lys Phe Val Phe Ser Thr Glu Glu Arg Thr Gln Leu Arg Leu Gly
    210                 215                 220

Ser Leu Glu Asp Thr His Ile Ile Lys Gly Glu Asp Asp Ala Leu Ser
225                 230                 235                 240

Asp Lys His Gly Cys Pro Ala Tyr Val Ser Pro Glu Ile Leu Asn Thr
                245                 250                 255

Thr Gly Thr Tyr Ser Gly Lys Ala Ala Asp Val Trp Ser Leu Gly Val
            260                 265                 270

Met Leu Tyr Thr Leu Trp Val Gly Arg Tyr Pro Phe His Asp Ser Asp
        275                 280                 285

Pro Ser Ala Leu Phe Ser Lys Ile Arg Arg Gly Gln Phe Cys Ile Pro
    290                 295                 300

Glu His Val Ser Pro Lys Ala Arg Cys Leu Ile Arg Ser Leu Leu Arg
305                 310                 315                 320

Arg Glu Pro Ser Glu Arg Leu Thr Ala Pro Gln Ile Leu Leu His Pro
                325                 330                 335

Trp Phe Glu Tyr Val Leu Glu Pro Gly Tyr Val Asp Ser Glu Ile Gly
            340                 345                 350

Thr Ser Asp Gln Ile Val Pro Glu Tyr Gln Glu Asp Ser Asp Ile Ser
        355                 360                 365

Ser Phe Phe Cys
    370

<210> SEQ ID NO 8
<211> LENGTH: 343
<212> TYPE: PRT
<213> ORGANISM: Mus musculus

<400> SEQUENCE: 8

Met Asn Ile His Arg Ser Thr Pro Ile Thr Ile Ala Arg Tyr Gly Arg
1               5                   10                  15

Ser Arg Asn Lys Thr Gln Asp Phe Glu Glu Leu Ser Ser Ile Arg Ser
                20                  25                  30

Ala Glu Pro Ser Gln Ser Phe Ser Pro Asn Leu Gly Ser Pro Ser Pro
            35                  40                  45

Pro Glu Thr Pro Asn Leu Ser His Cys Val Ser Cys Ile Gly Lys Tyr
        50                  55                  60

Leu Leu Leu Glu Pro Leu Glu Gly Asp His Val Phe Arg Ala Val His
65                  70                  75                  80

Leu His Ser Gly Glu Glu Leu Val Cys Lys Val Phe Glu Ile Ser Cys
```

```
                        85                  90                  95
Tyr Gln Glu Ser Leu Ala Pro Cys Phe Cys Leu Ser Ala His Ser Asn
            100                 105                 110

Ile Asn Gln Ile Thr Glu Ile Leu Leu Gly Glu Thr Lys Ala Tyr Val
        115                 120                 125

Phe Phe Glu Arg Ser Tyr Gly Asp Met His Ser Phe Val Arg Thr Cys
    130                 135                 140

Lys Lys Leu Arg Glu Glu Ala Ala Arg Leu Phe Tyr Gln Ile Ala
145                 150                 155                 160

Ser Ala Val Ala His Cys His Asp Gly Leu Val Leu Arg Asp Leu
                165                 170                 175

Lys Leu Arg Lys Phe Ile Phe Lys Asp Glu Glu Arg Thr Arg Val Lys
            180                 185                 190

Leu Glu Ser Leu Glu Asp Ala Tyr Ile Leu Arg Gly Asp Asp Asp Ser
        195                 200                 205

Leu Ser Asp Lys His Gly Cys Pro Ala Tyr Val Ser Pro Glu Ile Leu
    210                 215                 220

Asn Thr Ser Gly Ser Tyr Ser Gly Lys Ala Ala Asp Val Trp Ser Leu
225                 230                 235                 240

Gly Val Met Leu Tyr Thr Met Leu Val Gly Arg Tyr Pro Phe His Asp
                245                 250                 255

Ile Glu Pro Ser Ser Leu Phe Ser Lys Ile Arg Arg Gly Gln Phe Asn
            260                 265                 270

Ile Pro Glu Thr Leu Ser Pro Lys Ala Lys Cys Leu Ile Arg Ser Ile
        275                 280                 285

Leu Arg Arg Glu Pro Ser Glu Arg Leu Thr Ser Gln Glu Ile Leu Asp
    290                 295                 300

His Pro Trp Phe Ser Thr Asp Phe Ser Val Ser Asn Ser Gly Phe Gly
305                 310                 315                 320

Ala Lys Glu Ala Cys Asp Gln Leu Val Pro Asp Val Asn Met Glu Glu
                325                 330                 335

Asn Leu Asp Pro Phe Phe Asn
            340

<210> SEQ ID NO 9
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
cggaggactg tcctccg                                                    17

<210> SEQ ID NO 10
<211> LENGTH: 6
<212> TYPE: PRT
<213> ORGANISM: Artificial Sequence
<220> FEATURE:
<223> OTHER INFORMATION: Description of Artificial Sequence: Synthetic
      ATP binding site peptide
<220> FEATURE:
<221> NAME/KEY: MOD_RES
<222> LOCATION: (2)
<223> OTHER INFORMATION: Variable amino acid
<220> FEATURE:
<221> NAME/KEY: MOD_RES
<222> LOCATION: (4)..(5)
<223> OTHER INFORMATION: Variable amino acid
```

-continued

```
<400> SEQUENCE: 10

Gly Xaa Gly Xaa Xaa Gly
 1               5

<210> SEQ ID NO 11
<211> LENGTH: 8
<212> TYPE: PRT
<213> ORGANISM: Artificial Sequence
<220> FEATURE:
<223> OTHER INFORMATION: Description of Artificial Sequence: Synthetic
      illustrative peptide

<400> SEQUENCE: 11

Leu Arg Asp Leu Lys Leu Arg Arg
 1               5

<210> SEQ ID NO 12
<211> LENGTH: 8
<212> TYPE: PRT
<213> ORGANISM: Artificial Sequence
<220> FEATURE:
<223> OTHER INFORMATION: Description of Artificial Sequence: Synthetic
      consensus peptide

<400> SEQUENCE: 12

His Arg Asp Leu Lys Pro Glu Asn
 1               5

<210> SEQ ID NO 13
<211> LENGTH: 19
<212> TYPE: RNA
<213> ORGANISM: Unknown Organism
<220> FEATURE:
<223> OTHER INFORMATION: Description of Unknown Organism: Illustrative
      rat/mouse RNA sequence

<400> SEQUENCE: 13
cgagugagag augagccug                                          19

<210> SEQ ID NO 14
<211> LENGTH: 19
<212> TYPE: RNA
<213> ORGANISM: Homo sapiens

<400> SEQUENCE: 14
cgagcucgaa gugggcccc                                          19

<210> SEQ ID NO 15
<211> LENGTH: 11
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Gly Ser Arg Ser Arg Arg Pro Ser Tyr Arg Leu
 1               5                  10
```

PROTEIN KINASE B/AKT MODULATORS AND METHODS FOR THE USE THEREOF

RELATED APPLICATIONS

This application claims the benefit of U.S. Provisional Application Ser. No. 60/388,508, filed Jun. 12, 2002.

ACKNOWLEDGMENT

This invention was made with United States Government support under Grant No. GM-37828, awarded by the National Institutes of Health. The Government has certain rights in the invention.

FIELD OF THE INVENTION

The present invention relates to modulators of protein kinase B (PKB)/Akt protein kinases and methods for the use thereof. In a particular aspect, the invention relates to methods for disrupting the interaction between such modulators and PKB/Akt proteins, and the biological functions thereof, as well as compositions useful therefor.

BACKGROUND OF THE INVENTION

Under physiologic conditions, binding of insulin to the insulin receptor stimulates its intrinsic tyrosine kinase activity, leading to tyrosine phosphorylation of the insulin receptor substrates (IRS1 and IRS2) (Virkamaki et al., *J. Clin. Invest.* 103:931–943, 1999; White, *Mol. Cell. Biochem.* 182:3–11, 1998), and activation of downstream signaling pathways via the recruitment of cytoplasmic effector proteins containing SH2 domains which recognize tyrosine phosphorylated IRS proteins. For example, recruitment of the p85 subunit of the PI3K (Ruderman et al., *Proc. Natl. Acad. Sci. USA* 87:1411–1415, 1990) in response to insulin triggers a phospholipid dependent kinase cascade that culminates in the activation of a protein kinase B (PKB)/Akt (Brazil and Hemmings, *Trends Biochem. Sci.* 26:657–664, 2001). The activation of PI3K appears particularly critical for insulin signaling; most of the effects of insulin on glycogen synthesis and glucose transport are blocked in cells treated with PI3K inhibitors (Shepherd et al., *Biochem. J.* 305:25–28, 1995).

Diabetes mellitus is among the most common of all metabolic disorders, affecting up to 11% of the population by age 70. Type I diabetes (also referred to as insulin dependent diabetes mellitus or IDDM) represents about 5 to 10% of this group and is the result of a progressive autoimmune destruction of the pancreatic beta-cells with subsequent insulin deficiency.

There are two classes of type II diabetes (also referred to as non-insulin dependent diabetes mellitus or NIDDM). One typically presents in older people; thus it is sometimes called mature onset diabetes. Another form, though similar to mature onset, presents in a subject at a very early age. Type II diabetes represents 90–95% of the affected population, more than 100 million people worldwide (King and Zimmer, *Wld. Hlth. Statist. Quart.* 41:190–196, 1988; Harris et al., *Diabetes Care* 15:815–819, 1992), and is associated with peripheral insulin resistance, elevated hepatic glucose production, and inappropriate insulin secretion (DeFronzo, *Diabetes* 37:667–687, 1988). Family studies point to a major genetic component (Newman et al., *Diabetologia* 30:763–768, 1987; Kobberling, *Diabetologia* 7:46–49, 1971; Cook, *Diabetologia* 37:1231–1240, 1994). However, few susceptibility genes have been identified.

Type II diabetes is characterized by a patient's inability to respond to insulin and/or insufficient insulin secretion. Insulin exerts a dominant effect on the regulation of glucose homeostasis. In the liver, insulin inhibits the production of glucose by inhibiting gluconeogenesis and glycogenolysis. Insulin is thought to act by causing cells to absorb glucose from the blood stream. Once absorbed, the liver converts glucose to glycogen. The liver supplies glucose by converting glycogen stores to glucose. Insulin also has a major role in the regulation of protein and lipid metabolism through a variety of actions that affect the flux of protein and lipid substrates.

Key molecules in the regulation of insulin are the protein kinase B/Akt family of enzymes. The protein kinase B (PKB)/Akt kinases consists of at least three members (Akt1, Akt2, Akt3), collectively referred to herein as "Akt", that share extensive sequence homology but appear to perform distinct biological functions (Brazil and Hemmings, supra). Targeted disruption of Akt2, for example, leads to insulin resistance and glucose intolerance due to elevated hepatic gluconeogenesis and reduced glucose uptake in skeletal muscle (Cho et al., *Science* 292:1728–1731, 2001). By contrast, disruption of the Akt1 gene leads to growth retardation and apoptosis in certain tissues, with no apparent change in glucose homeostasis (Chen et al., *Genes Dev.* 15:2203–2208, 2001; Cho et al., *J. Biol. Chem.* 276:38349–38352, 2001). The mechanism underlying functional specification of Akt1 and Akt2 in liver and other tissues is unclear, but may involve subtle differences in substrate preference or in the ability of these kinases to associate preferentially with certain modulatory factors. In a recent study, Hemmings and coworkers described a C-terminal Akt modulatory protein, referred to as CTMP, that inhibits Akt activity at the plasma membrane and in the cytoplasm by binding to the C-terminal regulatory domain of Akt and blocking its phosphorylation at Thr308 and Ser473 (Maira et al., *Science* 294:374–380, 2001). Relative affinities of CTMP for Akt1 or Akt2 were not examined in this study, however.

Following activation in response to insulin, Akt inhibits glycogenolysis and promotes glycogen synthesis via direct phosphorylation of glycogen synthase kinase 3β at Ser9 (Brady et al., *J. Biol. Chem.* 273:14063–14066, 1998; Delcommenne et al., *Proc. Natl. Acad. Sci. USA* 95:11211–11216, 1998; Hajduch et al., *Diabetes* 47:1006–1013, 1998; Mitsuuchi et al., *J. Cell. Biochem.* 70:433–443, 1998; van Weeren, *J. Biol. Chem.* 273:13150–13156, 1998). Akt also appears to block gluconeogenic genes such as glucose-6-phosphatase and PEPCK, in part by phosphorylating and promoting nuclear export of members of the Forkhead family of transcriptional activators (Guo et al., *J. Biol. Chem.* 274:17184–17192, 1999; Kops et al., *Nature* 398:630–634, 1999; Nakae et al., *J. Biol. Chem.* 274:15982–15985, 1999). In recent studies, insulin has also been found to block gluconeogenesis by inhibiting the expression of the nuclear hormone coactivator PGC-1, although the underlying mechanism has not been elucidated (Herzig et al., *Nature* 413:179–183, 2001; Yoon et al., *Nature* 413:131–138, 2001).

In response to insulin stimulation, Akt is recruited to the plasma membrane via an interaction between its pleckstrin homology (PH) domain and phosphoinositol-(3, 4, 5)$P_3$ (PI3P), a product of phosphoinositol 1,3-dependent kinase (PI3K). Binding to PI3P is thought to promote a conformational change in Akt that renders the protein competent for subsequent activation events. Following binding to PI3P, Akt is phosphorylated at two residues: Thr308 within the active loop and Ser473 in the regulatory domain (Brazil and Hemmings, supra). Thr308 phosphorylation is mediated by the phosphoinositide-dependent kinase-1 (PDK-1) a PH domain kinase whose activity is also regulated by PI3K. Consistent with the importance of Thr308 phosphorylation for Akt catalytic activity, Akt activation is absent in PDK1−/−cells (Williams et al., *Curr. Biol.* 10:439–448, 2000). Ser 473 phosphorylation also contributes to Akt activation, although the identity of the Ser 473 Akt kinase is unknown.

By contrast with the well-characterized events leading to Akt activation, the mechanisms by which Akt activity is attenuated following insulin stimulation are less clear. Nevertheless, a number of upstream negative regulators have been identified; and the best characterized to date is the phosphatase-tensin homolog protein (PTEN), a potent lipid phosphatase that blocks Akt activation by dephosphorylating 3-phosphoinositides. PTEN is often mutated in a variety of sporadic cancers as well as in certain hamartoma syndromes; and tumors that harbor inactive PTEN correspondingly often contain elevated levels of Akt activity (Backman et al., *Nat. Genet.* 29:396–403, 2001; Ramaswamy et al., *Proc. Natl. Acad. Sci. USA* 96:2110–2115, 1999). In addition to PTEN, the SH2-containing inositol 5' phosphatase (SHIP), which hydrolyzes $PI(3,4,5)P_3$ to $PI(3,4)P_2$, has also been found to inhibit Akt activity; and SHIP −/−cells exhibit prolonged activation of Akt upon stimulation (Aman et al., *J. Biol. Chem.* 273:33922–33928, 1998; Liu et al., *Genes Dev.* 13:786–791, 1999).

Although lipid phosphatases constitute important upstream regulators of Akt, the Ser/Thr protein phosphatase 2A (PP2A) also appears to inhibit Akt via direct dephosphorylation of Thr308 and Ser473. In this regard, dephosphorylation and inactivation of Akt in response to hyperosmotic shock can be blocked by addition of calyculin, a relatively specific inhibitor of PP2A (Meier et al., *EMBO J.* 17:7294–7303, 1998). The degree to which PP2A contributes to Akt inactivation in vivo, however, is not well understood.

In the fed state, insulin promotes glucose homeostasis by stimulating glucose uptake in muscle and fat, and by blocking glucose production in liver (Saltiel and Kahn, *Nature* 414:799–806, 2001). Mice with an insulin receptor knockout in liver show glucose intolerance due in part to elevated glucose production (Michael et al., *Mol. Cell.* 6:87–97, 2000). Unchecked hepatic gluconeogenesis is an important contributor to fasting hyperglycemia in Type II diabetes, suggesting that the liver is a major site for glucose intolerance and insulin resistance in this disease.

In the fasted state, blood glucose levels are maintained through hepatic output of glucose, mediated predominantly by a fall in insulin and a rise in counter-regulatory hormones, i.e. glucagon (cAMP) and adrenal glucocorticoids. Glucagon promotes gluconeogenesis, in part, by stimulating the protein kinase A (PKA) mediated phosphorylation of the cAMP responsive element binding protein (CREB) (Imai et al., *J. Biol. Chem.* 268:5353–5356, 1993; Liu et al., *J. Biol. Chem.* 266:19095–19102, 1991; Quinn and Granner, *Mol. Cell. Biol.* 10:3357–3364, 1990). Expression of a dominant negative CREB inhibitor, referred to as A-CREB, in liver either acutely by infection with A-CREB Adenovirus, or chronically by transgenic expression in mice, causes hypoglycemia with reduced expression of all gluconeogenic genes (Herzig et al., supra). CREB was found to promote expression of the gluconeogenic program by stimulating expression of the nuclear hormone receptor coactivator PGC-1 (Herzig et al., supra; Yoon et al., supra) via a cAMP response element (CRE) site in the PGC-1 promoter. The ability of PGC-1 to promote expression of gluconeogenic genes in response to glucocorticoid signals likely explains the cooperativity between cAMP and glucocorticoid pathways in regulation of hepatic glucose production (Herzig et al., supra; Yoon et al., supra).

In addition to stimulating glucose output, chronic fasting has been found to induce insulin resistance in liver downstream of the insulin receptor. Indeed, glucocorticoids and, to a lesser extent, catecholamines, also induce hepatic insulin resistance by blocking post-receptor insulin signaling (Paez-Espinosa et al., *Mol. Cell. Endocrinol.* 156:121–129, 1999; Rao, *Metabolism* 44:817–824, 1995). The mechanism underlying insulin resistance in this setting remains obscure, but suggests the presence of an inducible negative signal that impairs insulin signaling under fasting conditions.

Thus, there remains a need in the art for methods to modulate enzymatic pathways in glucose regulation, particularly modulators of PKB/Akt kinases. Among other essential pathways in glucose regulation, these critical kinases inhibit glycogenolysis, promote glycogen synthesis, and block gluconeogenic genes. These pathways are all involved in diabetes mellitus, and modulators of PKB/Akt kinases present novel methods of diagnosis and treatment.

SUMMARY OF THE INVENTION

In accordance with the present invention, modulators of PKB/Akt protein kinases have been discovered to interact with PKB/Akt protein kinases, thereby affecting the phosphorylation state and activity of PKB/Akt protein kinases. The modulators, through their action on PKB/Akt protein kinases, play important roles in diverse physiological functions, including glucose regulation and anti-apoptosis.

In accordance with an aspect of the present invention, there are provided methods of screening test compounds to determine if any disrupt the interaction between a modulator of PKB/Akt protein and a PKB/Akt protein.

In accordance with another aspect of the present invention, there are provided methods for identifying compounds that disrupt the interaction between a modulator of PKB/Akt protein and a PKB/Akt protein.

In accordance with further aspects of the present invention, there are provided methods of determining if a subject has a predisposition to diabetes mellitus, insulin resistance or increased gluconeogenesis. Also provided are methods of determining if a subject is a candidate for Tribbles (TRB) family protein (collectively referred to as TRB) reducing therapy, wherein an elevated expression level of the modulator, relative to a normal individual, indicates that the subject is a candidate for TRB reducing therapy.

In accordance with another aspect of the present invention, there are provided methods of regulating cell survival, comprising contacting a biological system with an effective amount of an inhibitor of a TRB family protein.

In accordance with alternative aspects of the present invention, there are provided methods for screening and identifying test compounds which disrupt the interaction between a modulator of PKB/Akt protein with a PKB/Akt protein. Such methods use a GAL4 expression system.

In accordance with yet another aspect of the present invention, there are provided methods for screening test compounds to determine if any affect the phosphorylation state of a PKB/Akt protein kinase.

In accordance with further aspects of the present invention, there are provided various methods for treating diabetes mellitus. In a first method, a compound which inhibits production or activity of a modulator of PKB/Akt protein is administered to a subject in need thereof. In a second method, a compound which disrupts interaction of a modulator of PKB/Akt protein with a PKB/Akt protein is administered to a subject in need thereof. These methods may use compounds which are identified by the methods described herein.

In accordance with another aspect of the present invention, there are provided methods for modulating gluconeogenesis. These methods include contacting a biological system with an amount of an effective amount of a compound that modulates production or activity of a modulator of PKB/Akt protein.

BRIEF DESCRIPTION OF THE FIGURES

FIG. 1 shows the amino acid sequences of exemplary modulators of PKB/Akt proteins, the Akt-interacting protein TRB-3 (human (hum) (SEQ ID NO: 1 rat (SEQ ID NO: 2), mouse (mou) (SEQ ID NO: 3) shown) identified in a yeast two hybrid screen of a pro-adipocyte cDNA library. Similarities between other putative mammalian TRB family members (C5FW, C8FW) (SEQ ID NOs: 4 and 5, respectively), and Drosophila Tribbles (SEQ ID NO: 6) homologues are shown.

FIG. 2A shows the results of a mammalian two hybrid assay of HEK293 cells transfected with GAL4 Akt (ΔPH) or control GAL4 DNA binding domain (DBD) constructs. Co-transfection with TRB-3-VP16 or control VP16 construct are indicated.

FIG. 2B shows the results of GST pull down assays of $^{35}$S-labeled TRB-3 using GST-Akt or control GST sepharose resins. The lane marked INPUT shows 25% of total input of TRB-3 protein.

FIG. 2C shows the results of co-immunoprecipitation assays of HA-tagged Akt1 and FLAG-tagged TRB-3 proteins in transfected HEK293 cells. The top panel shows input of wild-type and alternately spliced ΔTRB-3 protein lacking conserved domain IX. The middle panel shows the results of a Western blot of HA-tagged Akt immunoprecipitates, showing that FLAG-tagged TRB-3 was recovered. The bottom panel shows input levels of HA-Akt in transfected cells.

FIG. 2D shows wild-type TRB-3 and putative alternative splice product (ΔTRB-3) lacking domain IX, which extends from amino acid residues 239–265.

FIG. 2E illustrates that TRB-3 co-localizes with Akt primarily in the cytoplasm. Fluorescence microscopy of CHO cells transfected with HA-tagged Akt and GFP-TRB-3 constructs is shown.

FIG. 2F show the results of Western blot analysis of Akt in immunoprecipates prepared from HepG2 cell extracts using either pre-immune (Pre), polyclonal anti-TRB-3 (αTRB-3) antiserum, or anti-TRB-3 antiserum blocked with TRB-3 polypeptide (amino acids 1–145). Recovery of a 60 kDa Akt immunoreactive band from each immunoprecipitate is shown. Input levels of TRB-3 and Akt are indicated.

FIG. 3A shows the results of a Western blot of phospho (Ser473) Akt, total Akt, and TRB-3 protein levels in human HepG2 hepatoma cells transfected with HA tagged Akt expression vectors plus increasing amounts of Flag tagged TRB-3 vector. Cells were either treated with insulin-like growth factor (IGF) (100 nM) or left untreated for 30 minutes.

FIG. 3B shows that TRB-3 blocks Akt catalytic activity. The results of an in vitro kinase assay of Akt immune complexes prepared from HepG2 cells transfected with TRB-3 expression vector and incubated with histone 2A substrate are shown. Relative incorporation of $^{32}$P-labeled as indicated in the bar graph was determined by phosphorimaging.

FIG. 3C shows that TRB-3 blocks pervanadate-dependent induction of Akt Ser473 phosphorylation. COS7 cells were transfected with Flag-tagged TRB-3 and HA tagged Akt. The bar graph indicates the levels of phospho (Ser473) Akt recovered from cells treated with Na pervanadate (100 µM) for 15 minutes or left untreated.

FIG. 3D shows the results of a transient assay of HepG2 cells transfected with Foxo1 regulated IGFBP-1 promoter plus constitutively active myristylated Akt (Myr-Akt) or mutant inactive Akt (KD-Akt) constructs. The reporter activity in cells treated with IGF or left untreated is shown. Cotransfection with wild-type or Akt-interaction defective TRB-3 (ΔC) is also indicated.

FIG. 3E illustrates inhibition of Akt kinase activity by TRB-3. In vitro kinase assays were done with Akt immunoprecipitates prepared from control or pervanadate-treated HEK293 cells transfected with HA-Akt1 and either control vector (GFP), wild-type TRB-3, or ΔTRB-3 (Δ). Kinase assays were performed using a consensus Akt peptide substrate. Treatment with sodium pervanadate (PV: 100 µM, 15 minutes) or vehicle is indicated.

FIG. 3F illustrates that disruption of TRB-3 expression potentiates insulin signaling via Akt in hepatocytes. Western blot assays of phospho Ser473 and total Akt levels as well as phospho Ser9 and total GSK-3β, and phospho Ser256 Foxo levels in control and insulin treated HepG2 cells transfected with wild-type (TRB-3) or mutant (CON) TRB-3 RNAi oligos are shown. Total levels of TRB-3 in HepG2 cells are also shown.

FIG. 3G illustrates interaction of TRB-3 with unphosphorylated Akt. The results of mammalian two hybrid assay of 293T cells transfected with GAL4-Akt constructs and either TRB3-VP16 or control VP16 expression vector are shown. The effect of mutating Thr308 in Akt to alanine or aspartate on the two hybrid interaction is also shown. Constructs expressing truncated Akt polypeptides (Δ145–240, Δ230–315, Δ315–390) are indicated. Comparable association of Akt 1 (WT) and Akt 2 with TRB-3 is also shown.

FIG. 4A shows the effect of wild-type and Akt interaction defective (Δ) TRB-3 on Foxo1 activity in HEK 293 cells transfected with IGF-binding protein 1 (IGFBP1) reporter containing 3 FKHR binding sites plus Foxo1 expression plasmid.

FIG. 4B shows the results of co-immunoprecipitation of endogenous TRB-3 with phospho Ser 473 Akt in FAO cells stimulated with IGF for 30 minutes. Western blot of phospho Akt immunoprecipates using polyclonal TRB-3 antiserum is also shown. Input levels of TRB-3 and phospho Akt from cell extracts are indicated.

FIG. 5A shows the results of a glucose output assay of FAO cells infected with TRB-3 or control adenovirus. The top panel shows the results of a Western blot of FAO extract from control and infected cells using anti-TRB-3 antiserum. Cells were treated with insulin ($10^{-7}$ M), dexamethasone and cAMP (D+F), or left untreated (con) as shown. Relative glucose output was measured after 3 hours.

FIG. 5B shows the results of a Western blot assay showing the effect of TRB-3 over-expression on phosphorylation of GSK-3β at Ser9 in FAO cells with treatments as indicated in FIG. 5A.

FIG. 5C in the top panel shows the results of a Western blot showing the effect of TRB-3 RNAi on levels of HA-tagged TRB-3 protein in transfected HepG2 cells. The bottom panel shows the effect of TRB-3 RNAi on PEPCK promoter activity in HepG2 cells treated with insulin, dexamethasone and cAMP, or left untreated. Control cells were transfected with mutant TRB-3 RNAi oligos containing two nucleotide substitutions.

FIG. 5D illustrates the effect of TRB-3 RNAi oligos on TRB-3 expression in hepatocytes. Human HepG2 hepatocytes were co-transfected with increasing amounts of TRB-3 RNA duplex oligos (0, 0.1, 0.2, 0.4 µg) plus Flag-tagged TRB-3 expression vector. Flag-tagged and endogenous TRB-3 expression in transfected cells was evaluated after 24 hours by Western blot assay.

FIG. 5E illustrates enhanced Akt phosphorylation in response to growth factor stimulation in cells with disrupted TRB-3 expression. Western blot assays of phospho Thr308 and total Akt levels in control and pervanadate (PV) treated HepG2 cells transfected with wild-type (WT) or mutant (mt) TRB-3 RNAi oligos and HA-tagged Akt expression vector. HepG2 extracts were probed with antiserum specific for phospho Thr308 (top) or non-discriminating Akt antiserum (middle) and TRB-3 antiserum (bottom).

FIG. 5F illustrates potentiation of GSK-3 phosphorylation in response to growth factor stimulation after RNAi-mediated disruption of TRB-3. Western blot assay of phospho Ser21 GSK-3α and phospho Ser9 GSK-3β in HepG2 hepatocytes transfected with TRB3 RNAi oligos and treated with pervanadate (PV) or vehicle as indicated. The effect of co-transfected mouse TRB-3 expression vector (which is not recognized by human TRB-3 RNAi oligos) on GSK-3 phosphorylation is also shown.

FIGS. 6A and 6B show the levels of TRB-3 mRNA in liver under fasting and refed conditions, relative to control mice fed ad libitum. Quantitative PCR analysis of total RNA from C57Bl6 (FIG. 6A) and Db/Db diabetic (FIG. 6B) mice (n=3 per group) normalized to RNA levels for GAPDH in the same samples is shown.

FIG. 6C shows the effect of TRB-3 over-expression on glucose homeostasis. Blood glucose levels in C57Bl6 male mice (6 week old) under fasting or refed conditions (n=7) are indicated. Mice were infected with control GFP or TRB-3-expressing adenovirus by tail vein injection, and glucose concentrations were monitored under refed conditions at times shown after infection.

FIG. 6D shows the results of Western blot analysis of TRB-3 protein amounts in whole liver extracts from wild-type and db/db mice using antiserum to TRB-3. Organs were harvested under refed or fasting (fast) conditions.

FIG. 7A shows the results of a glucose tolerance test of control and TRB-3 adenovirus infected mice. Mice were injected intraperitoneally with glucose (2 g/kg) and blood glucose levels were monitored at 30 minute intervals as indicated.

FIG. 7B shows the liver glycogen content in control GFP and TRB-3 adenovirus infected mice (n=4/group) under fed or fasted conditions.

FIG. 7C shows the serum insulin levels (ng/ml) in control (GFP) or TRB-3 adenovirus infected mice under refed or fasted conditions, as indicated.

FIG. 8A shows the results of a glucose output assay of FAO hepatoma cells infected with wild-type TRB-3, interaction defective ΔTRB-3 (Δ), or control (GFP) adenovirus. Cells were treated with insulin ($10^{-8}$ M) or left untreated for six hours. Relative inhibition of glucose output by insulin is indicated.

FIG. 8B shows the results of a Western blot assay showing effect of control GFP, wild-type TRB-3, and mutant ΔTRB-3 adenoviruses on phosphorylation of GSK-3β at Ser9 in FAO cells. Treatment with insulin or vehicle (C) is indicated. Total amounts of GSK-3 (α+β) and TRB-3 polypeptides are shown.

FIG. 8C illustrates a proposed model for TRB-3 action in liver. TRB-3 expression is induced under fasting conditions where it blocks insulin action by binding to Akt. Loss of Akt activity enhances glucose output from the liver in part by suppressing insulin dependent phosphorylation of GSK-3 by Akt.

FIG. 9 collectively shows modulation of TRB-3 expression and serum insulin levels. FIG. 9A shows that TRB-3 expression is induced by counter-regulatory hormones. The results of quantative PCR analysis of TRB-3 RNA levels in FAO hepatocytes treated with dexamethasone ($10^{-7}$ M) or forskolin (10 µM) for 18 hours are shown.

FIG. 9B shows the results of Western blot analysis of Akt in immunoprecipitates prepared from whole liver extracts of fasted db/db mice using either pre-immune (Pre), polyclonal anti-TRB-3 (αTRB-3) antiserum, or anti-TRB-3 antiserum blocked with TRB-3 polypeptide (amino acids 1–145). Recovery of a 60 kDa Akt immunoreactive band from each immunoprecipitate is shown. Input levels of TRB-3 and Akt are indicated.

FIG. 9C shows comparable expression of TRB-3 in db/db mice and in mice infected with TRB-3 adenovirus. Western blot assay of whole liver extracts using anti-TRB-3 or anti-CREB antiserum as control is shown. Livers were collected from db/db, TRB-3 adenovirus, or control GFP adenovirus infected mice.

DETAILED DESCRIPTION OF THE INVENTION

Figure 2:
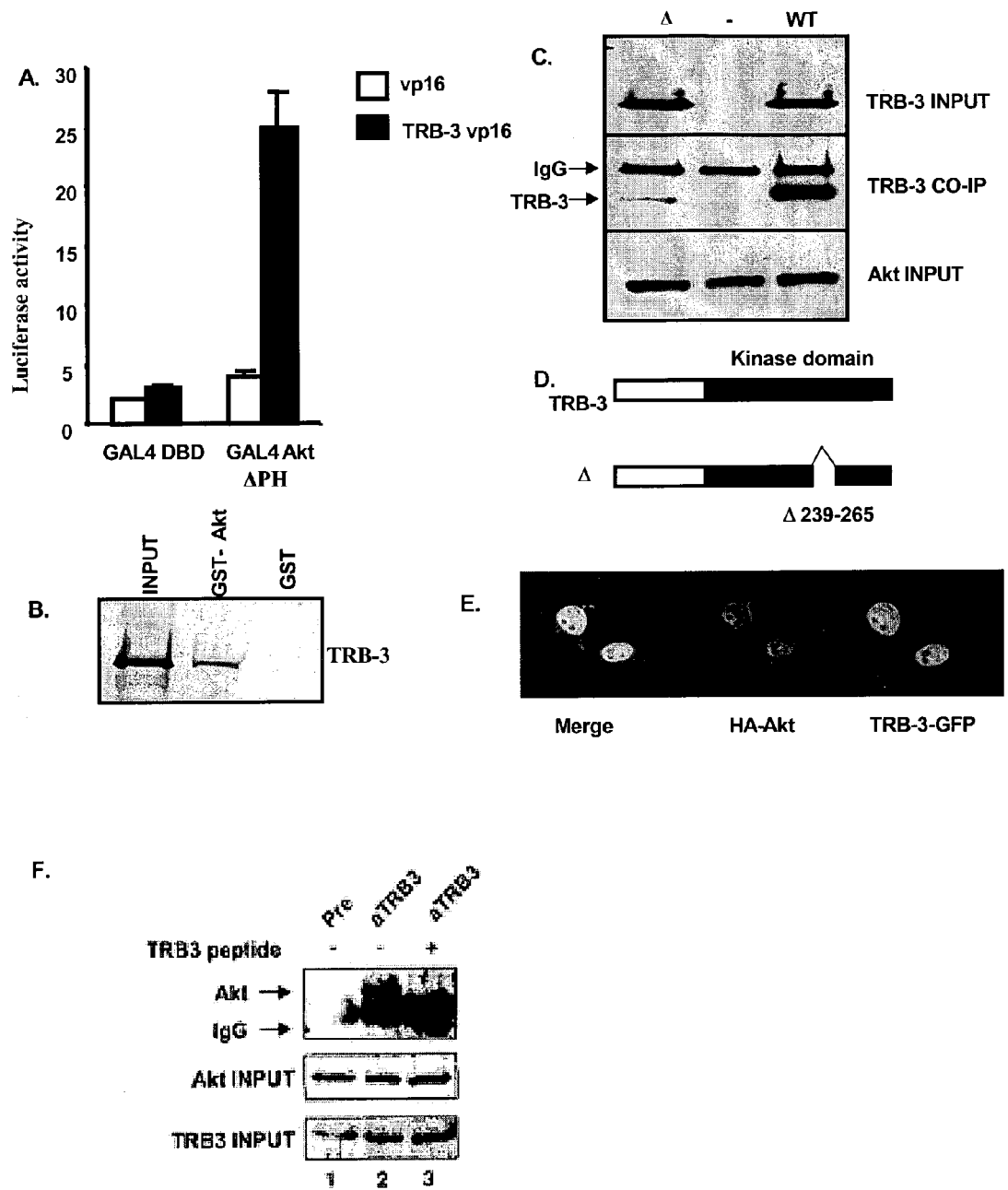
FIG. 2 collectively demonstrates that TRB-3 associates with Akt.

In accordance with the present invention, there are provided methods for screening test compounds to determine if any disrupt the interaction between a modulator of protein kinase B (PKB)/Akt protein and a PKB/Akt protein, said method comprising assaying for complex formation between said modulator protein and said PKB/Akt protein in the presence and absence of a test compound, wherein a decrease in the level of complex formation in the presence of said test compound, relative to complex formation in the absence of said test compound, is indicative of a compound which disrupts said interaction. In preferred embodiments the modulator is a TRB family protein member, such as TRB-3, C5FW, C8FW, TRB-1 or TRB-2.

The term "modulator of PKB/Akt protein", "modulator protein" or "modulator" as used herein, refers to a protein that is capable of altering a biological activity of a PKB/Akt kinase. Of particular interest are modulators that affect the ability of a PKB/Akt kinase to block genes involved in gluconeogenesis (such as glucose-6-phosphatase and PEPCK), to inhibit glycogenolysis (for example, by activating glycogen synthase kinase-3). Also of interest are modulators that affect the ability of a PKB/Akt kinase to protect cells from apoptosis. Modulators capable of altering a biological activity of PKB/Akt kinase may alter additional biological activities mediated by PKB/Akt kinases, which are known in the art (see, for example, Brazil and Hemmings, supra, for a recent review).

In preferred embodiments, the modulator contemplated for use in the practice of the present invention is a member of the TRB family, whose members contain highly conserved amino acid sequences. Exemplary modulators are provided herein, having the sequences listed in FIG. 1 and Table 1 below. The human TRB-3 protein is provided as SEQ ID NO:1; the rat TRB-3 protein as SEQ ID NO:2; and the mouse TRB-3 protein as SEQ ID NO:3. Other members of the TRB-3 family can readily be identified by homology to these sequences. For example, also provided are mammalian proteins C5FW (SEQ ID NO:4) and C8FW (SEQ ID NO:5), each of which contain extensive homology with TRB proteins. Non-mammalian proteins that share sequence homology with mammalian TRB family proteins are also considered members of the TRB family, for example, the *Drosophila* Tribbles protein (SEQ ID NO:6). The members of the TRB family are distinct from the previously identified Akt modulatory protein CTMP (Maira et al., supra). TRB-3 and its related family members TRB-1 and TRB-2 share 45% sequence similarity overall and bear strong resemblance to tribbles, a *Drosophila* protein that inhibits mitosis early in development by binding to the CDC25 homolog String and promoting its ubiquitination and proteasome-mediated degradation. Like tribbles, TRB family members have a truncated kinase domain that lacks an ATP binding site (GXGXXG; SEQ ID NO:10) and contains a variant catalytic core motif (TRB-3 amino acids 175–182; LRDLKLRR (SEQ ID NO:11) vs. consensus: HRDLKPEN (SEQ ID NO:12)). Correspondingly, tribbles and its mammalian counterparts lack detectable kinase activity by in vitro kinase assay.

TABLE 1

Members of the TRB protein family

Human TRB-3

MRATPLAAPA GSLSRKKRLE LDDNLDTERP VQKRARSGPQ PRLPPCLLPL SPPTAPDRAT AVATASRLGP

YVLLEPEEGG RAYQALHCPT GTEYTCKVYP VQEALAVLEP YARLPPHKHV ARPTEVLAGT QLLYAFFTRT

HGDMHSLVRS RHRIPEPEAA VLFRQMATAL AHCHQHGLVL RDLKLCRFVF ADRERKKLVL ENLEDSCVLT

GPDDSLWDKH ACPAYVGPEI LSSRASYSGK AADVWSLGVA LFTMLAGHYP FQDSEPVLLF GKIRRGAYAL

PAGLSAPARC LVRCLLRREP AERLTATGIL LHPWLRQDPM PLAPTRSHLW EAAQVVPDGL GLDEAREEEG

DREVVLYG (SEQ ID NO:1)

Rat TRB-3

MRATSLAASA DVPCRKKPLE FDDNIDVECP VLKRVRDEPE PGPTPSLPPA SDLSPAVAPA TRLGPYILLE

REQGNCTYRA LHCPTGTEYT CKVYPASEAQ AVLAPYARLP THQHVARPTE VLLGSQLLYT FFTKTHGDLH

SLVRSRRGIP EPEAAALFRQ MASAVAHCHK HGLILRDLKL RRFVFSNCER TKLVLENLED ACVMTGPDDS

LWDKMACPAY VGPEILSSRP SYSGRAADVW SLGVALFTML AGRYPFQDSE PALLFGKIRR GTFALPEGLS

ASARCLIRCL LRREPSERLV ALGILLHPWL REDCSQVSPP RSDRREMDQV VPDGPQLEEA EEGEVGLYG (SEQ ID NO:2)

House TRB-3

MRATPLAASA DVSCRKKPLE FDDNIDAKCP VLKRVRDEPE PGPLPSLLPP SPPPASDLSP AVAPATRLGP

YILLEREQGS VLGETKAYVF FEKSFGDMHS YVRSRKRLRE EEAAGLFRQM ASAVAHCHKH GLVLRDLKLR

RFVFSNCERT KLVLENLEDA CVMTGSDDSL WDKHACPAYV GPEILSSRPS YSGKAADVWS LGVALFTMLA

GRYPFHDSEP VLLFGKIRRG TFALPEGLSA PARCLIRCLL RKEPSERLVA LGILLHPWLR EDHGRVSPPQ

SDRREMDQVV PDGPQLEEAE EGEVGLYG (SEQ ID NO:3)

C5FW

IGKYLLLEPL EGDTGVYENL HTYIRHAKRL CETEARRLFY QIASAVAHCH DGGLVLRDLK LRKFIFKDEE

RTRVKLESLE DAYILRCDDD SLSDKHGCPA YVSPEILNTS GSYSGKAADV WSLGVMLYTM LVGRYPFHDI

EPSSLFSKIR RGQFNIPETL SPKAKCLIRS ILRREPSERL TSQEILDHPW FSTDFSVSNS GYGAKEVSDQ

LVPD (SEQ ID NO:4)

C8FW

TABLE 1-continued

Members of the TRB protein family

RLFKQIVSAV AHCHQSAIVL GDLKLRKFVF STEERTQLRL ESLEDTHIMK GEDDALSDKH GCPAYVSPEI

LNTTGTYSGK AADVWSLGVM LYTLLVGRYP FHDSDPSALF SKIRRGQFCI PEHISPKARC LIRSLLRREP

SERLTAPEIL LHPWFESVLE PGYIDSEIGT SDQIVPE (SEQ ID NO:5)

Drosophila Tribbles

AIFHQICQTV QVCHRNGIIL RDLKLRRFYF IDEARTKLQY ESLEGSMILD GEDDTLSDKI GCPLYTAPEL

LCPQQTYKGK PADMWSLGVI LYTMLVGQYP FYEKANCNLI TVIRHGNVQI PLTLSKSVRW LLLSLLRKDY

TERMTASHIF LTPWLRE (SEQ ID NO:6)

Mouse TRB-1

MRVGPVRFAL SGASQPRGPG LLFPAARGTP AKRLLDTDDA GAVAAKCPRL SECSSPPDYL SPPGSPCSPQ

PPPSTQGTGG SCVSSPGPSR IADYLLLPLA EREHVSRALC IHTGRELRCK EFPIKHYQDK IRPYIQLPSH

SNITGIVEVL LGESKAYVFF EKDFGDMHSY VRSRKRLREE EAARLFKQIV SAVAHCHQSA IVLGDLKLRK

FVFSTEERTQ LRLGSLEDTH IIKGEDDALS DKHGCPAYVS PEILNTTGTY SGKAADVWSL GVMLYTLWVG

RYPFHDSDPS ALFSKIRRGQ FCIPEHVSPK ARCLIRSLLR REPSERLTAP QILLHPWFEY VLEPGYVDSE

IGTSDQIVPE YQEDSDISSF FC (SEQ ID NO:7)

House TRB-2

MNIHRSTPIT IARYGRSRNK TQDFEELSSI RSAEPSQSFS PNLGSPSPPE TPNLSHCVSC IGKYLLLEPL

EGDHVFRAVH LHSGEELVCK VFEISCYQES LAPCFCLSAH SNINQITEIL LGETKAYVFF ERSYGDMHSF

VRTCKKLREE EAARLFYQIA SAVAHCHDGG LVLRDLKLRK FIFKDEERTR VKLESLEDAY ILRGDDDSLS

DKHGCPAYVS PEILNTSGSY SGKAADVWSL GVMLYTMLVG RYPFHDIEPS SLFSKIRRGQ FNIPETLSPK

AKCLIRSILR REPSERLTSQ EILDHPWFST DFSVSNSGFG AKEACDQLVP DVNMEENLDP FFN (SEQ ID NO:8)

TRB family members contemplated for use in the practice of the present invention include naturally occurring proteins, as well as those which are recombinantly or synthetically synthesized. Polypeptide or protein fragments are also contemplated for use in the practice of the present invention. Fragments can have the same or substantially the same amino acid sequence as the naturally occurring protein. A polypeptide or peptide having substantially the same sequence means that an amino acid sequence is largely, but not entirely, the same, but retains a functional activity of the sequence to which it is related. In general, polypeptides contemplated for use in the practice of the present invention include peptides, or full-length protein, that contain substitutions, deletions, or insertions into the protein backbone, that would still have an approximately 70%–90% homology to the original protein over the corresponding portion. A yet greater degree of departure from homology is allowed if like-amino acids, i.e. conservative amino acid substitutions, do not count as a change in the sequence.

A polypeptide may be substantially related but for a conservative variation, such polypeptides being encompassed by the invention. A conservative variation denotes the replacement of an amino acid residue by another, biologically similar residue. Examples of conservative variations include the substitution of one hydrophobic residue such as isoleucine, valine, leucine or methionine for another, or the substitution of one polar residue for another, such as the substitution of arginine for lysine, glutamic for aspartic acids, or glutamine for asparagine, and the like. Other illustrative examples of conservative substitutions include the changes of alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine, glutamine, or glutamate; methionine to leucine or isoleucine; phenylalanine to tyrosine, leucine or methionine; serine to threonine; threonine to serine; tryptophan to tyrosine; tyrosine to tryptophan or phenylalanine; valine to isoleucine or leucine; and the like.

Modifications and substitutions are not limited to replacement of amino acids. For a variety of purposes, such as increased stability, solubility, or configuration concerns, one skilled in the art will recognize the need to introduce, (by deletion, replacement, or addition) other modifications. Examples of such other modifications include incorporation of rare amino acids, dextra-amino acids, glycosylation sites, cytosine for specific disulfide bridge formation, and the like. The modified peptides can be chemically synthesized, or the isolated gene can be site-directed mutagenized, or a synthetic gene can be synthesized and expressed in bacteria, yeast, baculovirus, tissue culture and so on.

The term "variant" refers to polypeptides modified at one or more amino acid residues yet still retain their biological activity. Variants can be produced by any number of means known in the art, including, for example, methods such as, for example, error-prone PCR, shuffling, oligonucleotide-directed mutagenesis, assembly PCR, sexual PCR mutagenesis, and the like, as well as any combination thereof.

By "substantially identical" or "highly conserved" is meant a polypeptide or nucleic acid exhibiting at least 50%, preferably 60%, more preferably 70%, more preferably 80%, more preferably 85%, more preferably 90%, and most preferably 95% homology to a reference amino acid or nucleic acid sequence.

Sequence homology and identity are often measured using sequence analysis software (e.g., Sequence Analysis Software Package of the Genetics Computer Group, University of Wisconsin Biotechnology Center, 1710 University Avenue, Madison, Wis. 53705). The term "identity" in the context of two or more nucleic acids or polypeptide sequences, refers to two or more sequences or subsequences that are the same or have a specified percentage of amino acid residues or nucleotides that are the same when compared and aligned for maximum correspondence over a comparison window or designated region as measured using any number of sequence comparison algorithms or by manual alignment and visual inspection. The term "homology" in the context of two or more nucleic acids or polypeptide sequences, refers to two or more sequences or subsequences that are homologous or have a specified percentage of amino acid residues or nucleotides that are homologous when compared and aligned for maximum correspondence over a comparison window or designated region as measured using any number of sequence comparison algorithms or by manual alignment and visual inspection. Programs as mentioned above allow for amino acid substitutions with similar amino acids to determine a degree of homology between the sequences being compared.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequence for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Person & Lipman, *Proc. Natl. Acad. Sci. USA* 85:2444 (1988), by computerized implementations of these algorithms (GAP, BESTFIT, FASTA, and TFASTA in the Wisconsin Genetics Software Package, *Genetics Computer Group*, 575 Science Dr., Madison, Wis.), or by manual alignment and visual inspection.

Other algorithms for determining homology or identity include, for example, in addition to a BLAST program (Basic Local Alignment Search Tool at the National Center for Biological Information), ALIGN, AMAS (Analysis of Multiply Aligned Sequences), AMPS (Protein Multiple Sequence Alignment), ASSET (Aligned Segment Statistical Evaluation Tool), BANDS, BESTSCOR, BIOSCAN (Biological Sequence Comparative Analysis Node), BLIMPS (BLocks IMProved Searcher), FASTA, Intervals & Points, BMB, CLUSTAL V, CLUSTAL W, CONSENSUS, LCONSENSUS, WCONSENSUS, Smith-Waterman algorithm, DARWIN, Las Vegas algorithm, FNAT (Forced Nucleotide Alignment Tool), Framealign, Framesearch, DYNAMIC, FILTER, FSAP (Fristensky Sequence Analysis Package), GAP (Global Alignment Program), GENAL, GIBBS, GenQuest, ISSC (Sensitive Sequence Comparison), LALIGN (Local Sequence Alignment), LCP (Local Content Program), MACAW (Multiple Alignment Construction & Analysis Workbench), MAP (Multiple Alignment Program), MBLKP, MBLKN, PIMA (Pattern-Induced Multi-sequence Alignment), SAGA (Sequence Alignment by Genetic Algorithm) and WHAT-IF. Such alignment programs can also be used to screen genome databases to identify polynucleotide sequences having substantially identical sequences. A number of genome databases are available, for example, a substantial portion of the human genome is available as part of the Human Genome Sequencing Project (J. Roach, accessible on the world wide web (www) at the URL "weber.u.Washington.edu/~roach/human_genome_progress2.html") (Gibbs, 1995). Several databases containing genomic information annotated with some functional information are maintained by different organization, and are accessible via the internet on the world wide wed (www), for example, at the URL "tigr.org/tdb"; "genetics.wisc.edu"; "genome-www.stanford.edu/~ball"; "hiv-web.lanl.gov"; "ncbi.nlm.nih.gov"; "ebi.ac.uk"; "Pasteur.fr/other/biology"; and "genome.wi.mit.edu".

One example of a useful algorithm is BLAST and BLAST 2.0 algorithms, which are described in Altschul et al., *Nucl. Acids Res.* 25:3389–3402 (1977), and Altschul et al., *J. Mol. Biol.* 215:403–410 (1990), respectively. Software for performing BLAST analyses is publicly available through the National Center for Biotechnology Information (available on the world wide web (www) at the URL "ncbi.nlm.nih.gov"). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4 and a comparison of both strands. For amino acid sequences, the BLASTP program uses as defaults a wordlength of 3, and expectations (E) of 10, and the BLOSUM62 scoring matrix (see Henikoff & Henikoff, *Proc. Natl. Acad. Sci. USA* 89:10915 (1989)) alignments (B) of 50, expectation (E) of 10, M=5, N=−4, and a comparison of both strands.

The BLAST algorithm also performs a statistical analysis of the similarity between two sequences (see, e.g., Karlin & Altschul, *Proc. Natl. Acad. Sci. USA* 90:5873 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

In one embodiment, protein and nucleic acid sequence homologies are evaluated using the Basic Local Alignment Search Tool ("BLAST"). In particular, five specific BLAST programs are used to perform the following task:

(1) BLASTP and BLAST3 compare an amino acid query sequence against a protein sequence database;

(2) BLASTN compares a nucleotide query sequence against a nucleotide sequence database;

(3) BLASTX compares the six-frame conceptual translation products of a query nucleotide sequence (both strands) against a protein sequence database;

(4) TBLASTN compares a query protein sequence against a nucleotide sequence database translated in all six reading frames (both strands); and (5) TBLASTX compares the six-frame translations of a nucleotide query sequence against the six-frame translations of a nucleotide sequence database.

The BLAST programs identify homologous sequences by identifying similar segments, which are referred to herein as "high-scoring segment pairs," between a query amino or nucleic acid sequence and a test sequence which is preferably obtained from a protein or nucleic acid sequence database. High-scoring segment pairs are preferably identified (i.e., aligned) by means of a scoring matrix, many of which are known in the art. Preferably, the scoring matrix used is the BLOSUM62 matrix (Gonnet et al., Science 256:1443–1445 (1992); Henikoff and Henikoff, Proteins 17:49–61 (1993)). Less preferably, the PAM or PAM250 matrices may also be used (see, e.g., Schwartz and Dayhoff, eds., *Matrices for Detecting Distance Relationships: Atlas of Protein Sequence and Structure*, Washington: National Biomedical Research Foundation (1978)). BLAST programs are accessible through the U.S. National Library of Medicine, e.g., available on the world wide web (www) at the URL "ncbi.nlm.nih.gov".

The parameters used with the above algorithms may be adapted depending on the sequence length and degree of homology studied. In some embodiments, the parameters may be the default parameters used by the algorithms in the absence of instructions from the user.

As used herein, a PKB/Akt protein may similarly be a natural or synthesized member of the PKB/Akt family of protein kinases. Three main mammalian isoforms of this protein kinase family are well known in the art; PKBα/Akt1, PKBβ/Akt2, and PKBγ/Akt3. For a recent review of the field of the PKB/Akt family, see Brazil and Hemmings, *TIBS* 26:657–664, 2001. Also included are variants, variations, substitutions, modifications, and fragments as described above.

In addition to identifying modulators via homology to TRB family members, additional modulator of PKB/Akt proteins may be identified according to the methods described herein, for example, using a yeast two hybrid assay as described in Example 1.

The term "interaction" as used herein generally refers to a physical association of a modulator protein with a PKB/Akt protein. An interaction may be detected directly through assaying for complex formation between the two proteins, or indirectly through a resultant function, such as the ultimate expression and detection of a reporter gene. In order to study the interaction of a modulator protein and a PKB/Akt protein, they may be brought together in vitro or in vivo. For use in vitro, the proteins may be purified, synthesized, or expressed recombinantly as is known in the art. For use in vivo, the proteins may be expressed simultaneously in the same cell, for example in a functional bioassay. One or both proteins may be endogenous to a cell and one or both may be recombinantly introduced for expression in the same cell.

The term "disrupt" as used herein in relation to an interaction between two proteins, refers to the physical or functional interference with complex formation between the proteins. A compound may disrupt the interaction between a modulator protein and a PKB/Akt protein by blocking or inhibiting the initial association or contact between the two proteins, or by causing the disruption of the association resulting in the separation of the two proteins before a functional product of the association is produced, for example, phosphorylation of the PKB/Akt protein. The term "compound" as used herein refers to any molecule, including, but not limited to, nucleic acids, proteins, small molecules, drugs, and the like. The end result of a disruption by the compound is to cause loss or reduction of the normal function of the modulator protein.

As used herein, the term "purified" means that the molecule is substantially free of contaminants normally associated with a native or natural environment. A modulator protein and a PKB/Akt protein, or functional fragments of one or both thereof, useful in the practice of the present invention, can be obtained by a number of methods, e.g., precipitation, gel filtration, ion-exchange, reversed-phase, affinity chromatography, and the like. Other well-known methods are described in Deutscher et al., GUIDE TO PROTEIN PURIFICATION: METHODS IN ENZYMOLOGY Vol. 182, (Academic Press, 1990), which is incorporated herein by reference.

Alternatively, a purified protein, or functional fragment thereof, useful in the practice of the present invention, can also be obtained by well-known recombinant methods as described, for example, in Ausubel et al., CURRENT PROTOCOLS IN MOLECULAR BIOLOGY (Greene Publishing Associates, Inc. and John Wiley & Sons, Inc., 1993), also incorporated herein by reference. An example of recombinant means to prepare a protein, or functional fragments thereof, is to express nucleic acid encoding the protein, or functional fragment thereof, in a suitable host cell, such as a bacterial, yeast, insect or mammalian cell, using methods well known in the art, and recovering the expressed protein, again using methods well known in the art.

For example, expression vector systems may be used to produce cells expressing proteins or fragments thereof. Such vectors comprise the regulatory elements necessary for expression of the DNA in bacterial, yeast, insect, mammalian or animal cells, and the like. Regulatory elements are positioned relative to the DNA encoding the polypeptide of interest so as to permit expression thereof. Regulatory elements required for expression include promoter sequences to bind RNA polymerase and transcription initiation sequences for ribosome binding. For example, a bacterial expression vector includes a promoter such as the lac promoter and the Shine-Dalgarno sequence and the start codon AUG (Ausubel et al., supra) for transcription initiation. Similarly a eukaryotic expression vector includes a heterologous or homologous promoter for RNA polymerase II, a downstream polyadenylation signal, the start codon AUG, and a termination codon for detachment of the ribosome. Such vectors can readily be obtained commercially or assembled by methods well known in the art.

Proteins and biologically active fragments thereof, useful in the practice of the present invention can also be produced by chemical synthesis. Synthetic polypeptides can be produced, for example, using Applied Biosystems, Inc. Model 430A or 431A automatic polypeptide synthesizer and chemistry provided by the manufacturer.

The term "screening" as used herein refers to determining whether or not a test compound has the effect of interest, specifically disrupting the interaction between a modulator protein and a PKB/Akt protein. In order to screen a test compound, one performs an assay in the presence and in the absence of the test compound, and compares the results of the two assays. For example, one may assay for complex formation by combining a modulator protein with a PKB/Akt protein and a test compound; combining a modulator protein with a PKB/Akt protein without the test compound; and comparing the level of complex formation in the presence of the test compound, relative to the level of complex formation in the absence of the test compound. A decrease in the level of complex formation in the presence of the test compound would be indicative of a compound that disrupts the interaction between the modulator and the PKB/Akt proteins examined. An insignificant change in the level of complex formation in the presence of the test compound would be indicative of a compound that has no effect on the interaction examined.

The level of complex formation between a modulator protein and a PKB/Akt protein may be assayed by various methods known to one skilled in the art. Preferred methods employ the use of conjugates, tag moieties (such as GST, histidine, HA, FLAG and the like) or antibodies for one partner of the complex to isolate the associated complex of the two proteins from non-associated proteins, followed by detection of the second partner in the isolated complex. For example, cell lysates of cells containing recombinantly expressed and tagged Akt and TRB proteins may be co-immunoprecipitated and examined by Western blot analysis to determine the level of complex formation (see, for example, Example 2 and FIG. 2C). Other comparable methods include various standard immunoprecipitation techniques, GST or HIS pull down assays, immunofluorescence, Western blot analysis, mass spectrometry, and the like.

According to another aspect of the present invention, there are provided methods for identifying a compound that disrupts the interaction between a modulator of PKB/Akt protein and a PKB/Akt protein, said method comprising contacting said modulator and said PKB/Akt protein in the presence and absence of a test compound, and determining whether said test compound decreases the level of complex formation between said modulator and said PKB/Akt protein, relative to the level of complex formation in the absence of said test compound, thereby identifying a compound that disrupts said interaction.

The term "identifying" as used herein, refers generally to the positive identification of a compound which meets the criteria set forth herein using invention methods. In this context, a positive compound is a compound that disrupts the interaction between a modulator protein and a PKB/Akt protein. The method of identification employs the same types of compositions and systems as described above, to achieve a determination of a decreased level of complex formation between the modulator and the PKB/Akt protein in the presence of the test compound.

According to an alternative embodiment, the present invention further provides methods for screening test compounds to determine if any disrupt the interaction between a modulator of PKB/Akt protein with a PKB/Akt protein, said method comprising:

(a) contacting a modified host cell with a test compound, wherein said modified host cell comprises:
  (i) a first fusion protein comprising a GAL4 DNA binding domain, operatively associated with a PKB/Akt protein or a functional fragment thereof,
  (ii) a second fusion protein comprising an activation domain, operatively associated with a modulator of PKB/Akt protein or a functional fragment thereof, and
  (iii) a reporter construct comprising a GAL4 response element operatively linked to a reporter gene; and
(b) determining the expression level of said reporter gene; wherein a reduced expression level of said reporter gene product in the presence of said test compound is indicative of a compound that disrupts said interaction.

Various constructs employed in the practice of the present invention are well known in the art. Thus, the GAL4 DNA binding domain, the activation domain and GAL4 response elements have all been well characterized and extensively discussed in the art. For example, the DNA binding domain of the yeast GAL4 protein comprises at least the first 74 amino acids thereof (see, for example, Keegan et al., *Science* 231:699–704, 198). Preferably, the first 90 or more amino acids of the GAL4 protein will be used, with the first 147 amino acid residues of yeast GAL4 being presently most preferred.

Activation domains contemplated for use in the practice of the present invention are well known in the art and can readily be identified by the artisan. Examples include the GAL4 activation domain, BP64, VP16, and the like. Exemplary GAL4 response elements are those containing the palindromic 17-mer: 5'-CGGAGGACTGTCCTCCG-3' (SEQ ID NO:9); such as, for example, 17MX, as described by Webster et al., *Cell* 52:169–178,1988, as well as derivatives thereof. Additional examples of suitable response elements include those described by Hollenberg and Evans, *Cell* 55:899–906, 1988; or Webster et al., *Cell* 54:199–207, 1988.

As used herein, the phrase "operatively associated with" means that the respective DNA sequences (represented, for example, by the terms "GAL4 response element" and "reporter gene") are operational, i.e., work for their intended purposes; the word "functionally" means that after the two segments are linked, upon appropriate activation by a ligand-receptor complex, the reporter gene will be expressed as the result of the fact that the corresponding "response element" was "turned on" or otherwise activated.

As employed herein, the term "reporter construct" refers to a recombinant construct, for example, an expression vector comprising a reporter gene under the control of a signal dependent transcription factor. In yet another example, the term refers to an expression vector comprising a reporter gene under the control of GAL4 response element. Activation of a target gene induces the reporter gene to express an exogenous identifiable "signal". Expression of the reporter gene indicates that the target gene has been modulated. Exemplary reporter genes encode luciferase, β-galactosidase, chloramphenicol transferase, and the like.

In accordance with the present invention, expression of the reporter gene can be monitored in a variety of ways. Preferably, the expression of the reporter gene itself provides a readily detectable and measurable output, for example, luminescence or fluorescence. Other methods produce an enzymatic product that is detectable by providing the appropriate substrate, for example, β-galactosidase. Immunological procedures are also useful for in vitro detection of a polypeptide produced by the reporter gene in a sample include immunoassays that employ a detectable antibody. Such immunoassays include, for example, ELISA, Pandex microfluorimetric assay, agglutination assays, flow cytometry, serum diagnostic assays, immunohistochemical staining procedures, and the like, which are well known in the art. An antibody can be made detectable by various means well known in the art. For example, a detectable marker can be directly or indirectly attached to the antibody. Useful markers include, for example, radionuclides, enzymes, fluorogens, chromogens and chemiluminescent labels.

The term "modified host cell" as used herein, refers to any cell that is transformed or transfected to contain constructs for the production of the required fusion proteins and reporter genes. Any cell line can be used as a suitable "host" for the functional bioassay contemplated for use in the practice of the present invention. Thus, cells contemplated for use in the practice of the present invention include transformed cells, non-transformed cells, neoplastic cells, primary cultures of different cell types, and the like. Exemplary cells which can be employed in the practice of the present invention include HEK 293 cells, Schneider cells, CV-1 cells, HuTu80 cells, F9 cells, NTERA2 cells, NB4 cells, HL-60 cells, 293 cells, Hela cells, yeast cells, NIH3T3 cells, and the like. The above-described cells (or fractions thereof are maintained under physiological conditions when contacted with physiologically active compound. "Physiological conditions" are readily understood by those of skill in the art to comprise an isotonic, aqueous nutrient medium at a temperature of about 37° C.

According to another alternative embodiment, the present invention further provides methods for identifying a compound which disrupts the interaction between a modulator of PKB/Akt protein and a PKB/Akt protein, said method comprising:
(a) contacting a modified host cell with a test compound, wherein said modified host cell comprises:
  (i) a first fusion protein comprising a GAL4 DNA binding domain, operatively associated with a PKB/Akt protein or a functional fragment thereof,
  (ii) a second fusion protein comprising an activation domain, operatively associated with a modulator of PKB/Akt protein or a functional fragment thereof, and
  (iii) a reporter construct comprising a GAL4 response element operatively linked to a reporter gene; and
(b) determining whether said test compound decreases the expression of said reporter gene product, relative to expression of said reporter gene product in the absence of said test compound, thereby identifying a compound that disrupts said interaction.

According to another aspect of the present invention, there are provided methods of screening test compounds to determine if any affect the phosphorylation state of a PKB/Akt protein, said method comprising assaying for the phosphorylation level of said PKB/Akt protein in the presence of a modulator of PKB/Akt protein and a test compound relative to the phosphorylation level of said PKB/Akt protein in the presence of said modulator alone; wherein a change in said phosphorylation level is indicative of a compound that affects the phosphorylation state of said PKB/Akt protein.

As used herein, "phosphorylation state" refers to the level of phosphorylation of a specific protein. The protein may be phosphorylated at multiple sites, commonly at certain amino acid residues. A protein may be unphosphorylated, i.e., no sites bear a phosphate group, or a protein may be fully phosphorylated, i.e., all amino acids capable of being phosphorylated bear phosphate groups, or a protein may be partially phosphorylated, i.e., at least one, at least two, at least three or more amino acid residues capable of phosphorylation bear phosphate groups.

Figure 3:
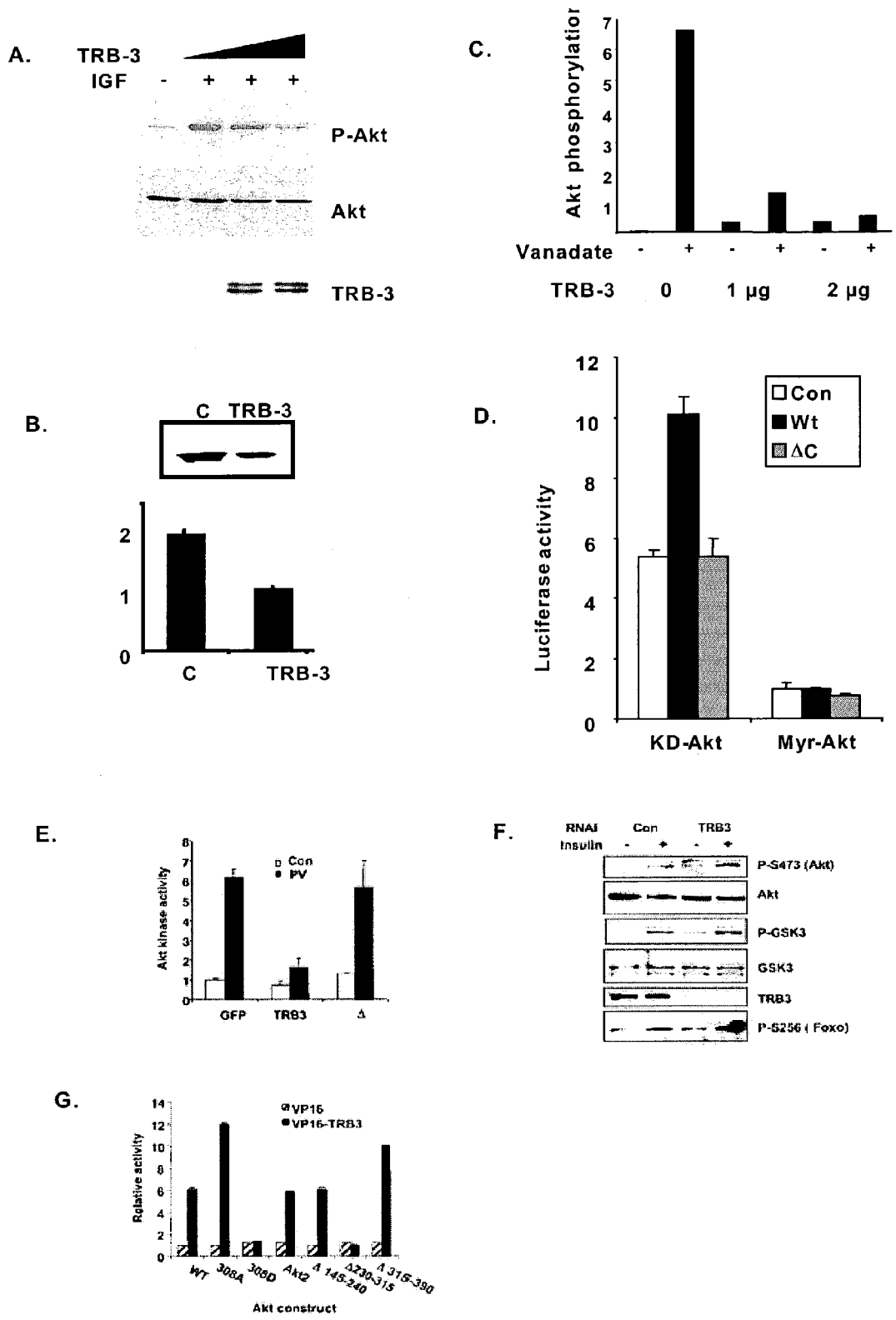
FIG. 3 collectively shows that TRB-3 inhibits growth factor dependent phosphorylation and activation of PKB/Akt.

The phosphorylation state of a PKB/Akt protein is determined by detecting the level of phosphorylation at certain amino acid residues. In preferred embodiments, the method detects the level of phosphorylation of Akt at amino acid Threonine 308 and/or amino acid Serine 473. The phosphorylation level can be conveniently detected using an antibody specific for a phosphorylated version of the protein (see, for example, Example 3 and FIG. 3A). A quantitative evaluation of the phosphorylation state can be achieved by varying the concentrations of the modulator protein and/or the test compound, wherein an increased concentration of an effective test compound causes a decrease in Akt phosphorylation by interfering with the activity of the modulator protein.

According to a further aspect of the present invention, there are provided methods of determining if a subject has a predisposition to diabetes mellitus, to insulin resistance or to increased gluconeogenesis. These invention methods comprise determining the expression level of a modulator of PKB/Akt protein in the subject, wherein an elevated expression level of said modulator, relative to a normal individual, is indicative of the indicated predisposition.

The term "predisposition" as used herein, refers to a preliminary signal that a subject is more likely than an average person to exhibit a disease or symptom of disease in the future. A "normal" individual, is a person that exhibits no signs or symptoms of abnormal glucose regulation or diabetes, and does not have a predisposition for diabetes or abnormal glucose regulation.

Diabetes and glucose regulation can be monitored by techniques known in the art, including a fasting plasma glucose test, an oral glucose tolerance test, a two-hour postprandial plasma glucose, and the like. Such determinations of diabetes rely on abnormalities in insulin levels or insulin function. Invention methods allow a determination of a predisposition to diabetes independent of insulin level or activity. Thus, invention methods can provide a determination of a predisposition for diabetes earlier, and prior to insulin insufficiency allowing a subject with a positive determination to take preventive steps to prevent progression of the disease, or to begin treatment earlier.

A Fasting Plasma Glucose (FPG) also known as a fasting blood sugar test is a carbohydrate metabolism test that measures plasma, or blood, glucose levels after a 12–14 hour fast. Fasting stimulates the release of the hormone glucagon, which in turn raises plasma glucose levels. In non-diabetic individuals the body will produce and process insulin to counteract the rise in glucose levels. In diabetics this does not happen, and the tested glucose levels will remain high. The "normal" range for results may vary according to the lab procedures used. When using the glucose oxidase and hexokinase methods, normal values are typically 70 to 100 mg/dl. Medications, exercise, and recent illnesses can impact the results of this test. Levels of 126 mg/dl or higher indicate a need for a subsequent retest and if the same levels are reached during the retest, diabetes mellitus is usually diagnosed. Results that measure only slightly above the normal range may require further testing, including the oral glucose tolerance test or the postprandial plasma glucose test, to confirm a diabetes diagnosis.

An Oral Glucose Tolerance Test, (OGTT) is a test that measures blood glucose levels four to five times over a 3-hour period. The subject is administered an oral dose of glucose solution (75 to 100 grams of an extremely sweet drink), which should cause glucose levels to rise in the first hour, and then fall back to normal within three hours as the body produces insulin to normalize glucose levels. Insulin production is monitored during the entire period, usually through blood samples. On average, normal glucose levels typically peak at 160–180 mg/dl from 30 minutes to 1 hour after administration of the oral glucose dose, and should then return to fasting levels of 140 mg/dl or less within a 2 to 3 hour period. Factors such as age, weight, and race can influence results, as can recent illnesses and certain medications. Glucose levels that quickly rise above normal levels (i.e., 200 mg/dl or higher) and take longer to normalize usually indicate diabetes mellitus.

A Two-Hour Postprandial Plasma Glucose is a blood test that measures the body's ability to metabolize carbohydrates and produce insulin. Generally, levels of less than 145 mg/dl are considered normal (when using the glucose oxidase or hexokinase laboratory methods). Normal results also vary by age. Individuals age 50 and older will have slightly higher levels than those under this age range. Two-hour postprandial glucose values of 200 mg/dl or higher indicate diabetes.

An average normal value for the expression level of a modulator protein may be obtained from a plurality of normal individuals. The average normal value, herein the expression level of a normal individual, can then be used as a comparison for the subject being tested. Typically, an "elevated" value would be a level of expression that is statistically greater than the average normal value.

Preferably, the expression level is the quantity of the modulator protein present. The quantity of a modulator protein may be measured using any method known in the art. Convenient methods of measuring a protein level use antibodies specific for the protein of interest, for example, immunoassay, ELISA, RIA, serum diagnostic assay, immunohistochemistry, and the like. Preferable samples for such measurements are readily obtainable from the subject to be tested, for example, blood samples, urine samples, lavage samples, and the like.

The disorder of diabetes mellitus as referred to herein encompasses Type I diabetes (also known as insulin dependent diabetes mellitus or IDDM); and Type II diabetes (also known as non-insulin dependent diabetes mellitus or NIDDM), both mature onset and early onset. Type II represents 90–95% of diabetics, and is associated with peripheral insulin resistance, elevated hepatic glucose production, and inappropriate insulin secretion. Insulin resistance, as used herein is associated with Type II diabetics, and is indicative of a person who would be non-responsive to insulin therapy for diabetes mellitus.

For example, in patients with non-insulin dependent diabetes mellitus (NIDDM), hyperglycemia develops, in part as a result of beta-cell failure secondary to chronic insulin resistance. This hyperglycemia appears to be exacerbated by hyperglucogonemia and increased hepatic gluconeogenesis. cAMP appears to be the major starvation state signal which triggers glucagon gene expression as well as transcription of PEPCK, the rate limiting enzyme in gluconeogenesis.

Hyperglycemia is associated with an increased risk for all of the common late complications of diabetes mellitus, which are the major causes of excess morbidity and mortality in diabetics. However, there is no generally applicable and consistently effective means of maintaining plasma glucose fluctuations within a normal range in diabetics, and efforts to do so entail significant risks of causing frequent or severe hypoglycemic episodes. Nevertheless, common treatments include diet management and the use of insulin preparations and oral hypoglycemic agents. Invention methods provide a monitor for potential resistance to insulin, and an indication that a patient may require alternative methods of therapy.

Accordingly, there are also provided methods of determining if a subject is a candidate for TRB reducing therapy. The method includes determining the expression level of a modulator of PKB/Akt protein in the subject, wherein an elevated expression of said modulator, relative to a normal individual, is indicative that said subject is a candidate for such therapy.

As used herein, the term "TRB reducing therapy" refers to decreasing the protein level of a modulator of PKB/Akt in the subject. Exemplary modulators include TRB-3, C5FW, C8FW, TRB-1 and TRB-2. In various embodiments, the method of reduction may involve decreasing levels of nucleic acids encoding a modulator of PKB/Akt, or decreasing the transcription, translation or stability of such nucleic acids, or decreasing the levels of PKB/Akt protein expression, activity or stability.

According to another aspect of the present invention, there are provided methods of regulating cell survival, comprising contacting a biological system with an effective amount of an inhibitor of a TRB family protein. TRB family proteins include, preferably, TRB-3. PKB/Akt family members are known to exhibit an anti-apoptotic function. As demonstrated herein, the TRB modulator affects the activation and subsequent biological functions of Akt. An inhibitor of a TRB modulator would disrupt the association of TRB with Akt, thereby interfering with the anti-apoptotoic function of Akt. Thus, the TRB family members may be used to regulate cell survival through an inhibitor of the TRB protein.

As used herein, the phrase "biological system" refers to an intact organism or a cell-based system, containing at least one modulator protein and at least one PKT/Akt protein. The term "contacting" as used herein refers to any method that brings the inhibitor into physical association with the biological system. For example, in a cell-based assay, the inhibitor may be introduced into the media containing the cells; in a whole organism, the inhibitor may be administered to the organism using any convenient route known in the art.

According to further aspects of the present invention, there are provided methods for treating diabetes mellitus, comprising administering to a subject in need thereof an effective amount of a compound that inhibits production or activity of a modulator of PKB/Akt protein. Alternatively, there are provided methods for treating diabetes mellitus, comprising administering to a subject in need thereof an effective amount of a compound that disrupts interaction of a modulator of PKB/Akt protein with a PKB/Akt protein.

Invention methods ameliorate hyperglycemia associated with diabetes mellitus by modulating gluconeogenesis and allowing PKB/Akt protein kinases to regulate gluconeogenic genes. In preferred embodiments, the subject is a mammal, most preferably a human, and the modulator is a TRB family protein as described herein.

Suitable preferred compounds include compounds that are identified by invention methods as disclosed herein. Invention compounds may alter RNA levels of a modulator. For example, a compound may be an antisense nucleotide directed against the modulator to decrease modulator DNA available for transcription or modulator RNA available for translation. Other compounds can readily be identified by one of skill in the art that would interfere with modulator DNA transcription or modulator RNA translation, for example, agents that interfere with transcription or translation factors, nucleotide binding moieties, RNA interference oligonucleotides, hairpin oligonucleotides, and the like.

Alternatively, invention compounds may alter protein levels of said modulator. This may be a result of altering RNA levels or interfering with translation into protein as above. Other compounds include antibodies that are specific for the modulator protein, or compounds that may sequester the modulator protein such that it is unavailable for complex formation with PKB/Akt proteins.

As employed herein, the phrase "effective amount" refers to levels of compound which provide an in vivo concentration sufficient to inhibit production or activity of a modulator, or to disrupt interaction of a modulator with a PKB/Akt protein. Such a concentration typically falls in the range of about 10 nM up to 2 µM; with concentrations in the range of about 100 nM up to 500 nM being preferred. Since the activity of different compounds described herein may vary considerably, and since individual subjects may present a wide variation in severity of symptoms, it is up to the practitioner to determine a subject's response to treatment and vary the dosages accordingly.

Compounds contemplated for use in the practice of the present invention can be administered in a variety of forms (e.g., in combination with a pharmaceutically acceptable carrier therefor) and by a variety of modes of delivery. Exemplary pharmaceutically acceptable carriers include carriers suitable for oral, intravenous, subcutaneous, intramuscular, intracutaneous, and the like administration. Administration in the form of creams, lotions, tablets, dispersible powders, granules, syrups, elixirs, sterile aqueous or non-aqueous solutions, suspensions or emulsions, and the like, is contemplated.

For the preparation of oral liquids, suitable carriers include emulsions, solutions, suspensions, syrups, and the like, optionally containing additives such as wetting agents, emulsifying and suspending agents, sweetening, flavoring and perfuming agents, and the like.

For the preparation of fluids for parenteral administration, suitable carriers include sterile aqueous or non-aqueous solutions, suspensions, or emulsions. Examples of non-aqueous solvents or vehicles are propylene glycol, polyethylene glycol, vegetable oils, such as olive oil and corn oil, gelatin, and injectable organic esters such as ethyl oleate. Such dosage forms may also contain-adjuvants such as preserving, wetting, emulsifying, and dispersing agents. They may be sterilized, for example, by filtration through a bacteria-retaining filter, by incorporating sterilizing agents into the compositions, by irradiating the compositions, or by heating the compositions. They can also be manufactured in the form of sterile water, or some other sterile injectable medium immediately before use.

In yet another embodiment of the present invention, there are provided methods for modulating gluconeogenesis. The method includes contacting a biological system with an effective amount of a compound which modulates production or activity of a modulator of PKB/Akt protein. The compounds mentioned herein and identified by the methods described herein are effective for preventing and treating various disorders of, for example, impaired glucose tolerance, diabetes (type II diabetes), diabetic complications (e.g., diabetic nephropathy, diabetic neuropathy, diabetic retinopathy, polycystic ovarian syndrome (PCOS), etc.), syndrome of insulin resistance (e.g., insulin receptor disorders, Rabson-Mendenhall syndrome, leprechaunism, Kobberling-Dunnigan syndrome, Seip syndrome, Lawrence syndrome, Cushing syndrome, acromegaly, obesity, psoriasis etc.), hyperlipidemia, coronary heart disease and other cardiovascular disorders including atherosclerosis, stenocardia, cardiac failure, etc.), hyperglycemia (e.g., abnormal saccharometabolism such as feeding disorders, etc.), and hypertension based on their blood sugar level-depressing activity, as well as stenocardia, hypertension, pulmonary hypertension, congestive heart failure, glomerulopathy (e.g., diabetic glomerulosclerosis, etc.), dyslipidaemia, tubulointerstitial disorders (e.g., renopathy induced by FK506, cyclosporin, etc.), renal failure, atherosclerosis, angiostenosis (e.g., after percutaneous arterioplasty), distal angiopathy, cerebral apoplexy, chronic reversible obstructions (e.g., bronchitis, asthma (chronic asthma, allergic asthma), etc.), allergic rhinitis, urticaria, glaucoma, diseases characterized by enteromotility disorders (e.g., hypersensitive enteropathy syndrome, etc.), impotence (e.g., organic impotence, psychic impotence, etc.), and diabetic complications (e.g., diabetic gangrene, diabetic arthropathy, diabetic glomerulosclerosis, diabetic dermatopathy, diabetic neuropathy, diabetic cataract, diabetic retinopathy, etc.), nephritis, cancerous cachexia, nephrotic syndrome, hypertensive nephrosclerosis, end-stage renal diseases and microalbuminuria as well as certain eating disorders, as aldose reductase inhibitors and for improving cognitive functions in dementia, and restenosis after PTCA based on their cGMP-PDE (especially PDE-V)-inhibiting activity, smooth muscle relaxing activity, bronchodilating activity, vasodilating activity, smooth muscle cell suppressing activity, and antiallergic activity, and the like, including diseases and disorders associated with aberrant or abnormal PCG-1, HNF and glucocorticoid (receptor).

The invention will now be described in greater detail by reference to the following non-limiting examples.

EXAMPLE 1

Identification of TRB Family Proteins

Using a human pre-adipocyte cDNA library (e.g., F322 A and F422A) in yeast two hybrid experiments, proteins were identified that associate with a GAL4 ΔPH (amino acids 150–480) Akt construct containing the catalytic and regulatory but not the pleckstrin homology domain (amino acids 1–145) of Akt1. 25 positives were obtained from a total of $2 \times 10^6$ clones. These clones encoded a 354 amino acid protein previously identified as a neuronal cell death inducible putative protein kinase (NIPK) of unknown function (Mayumi-Matsuda, *Biochem. Biophys. Res. Commun.* 258: 260–264, 1999); more recently designated TRB-3. The present invention identifies a family of proteins, termed Tribble family proteins (collectively TRB; of which NIPK is a member), as modulators of PKB/Akt kinases. Members of this family are highly conserved between human, rat, and mouse species (see FIG. 1, SEQ ID NO:1, 2 and 3, respectively), containing conserved kinase subdomains VIB–XI (see Hanks and Hunter, *FASEB J.* 9:576–596, 1995, for a review of domain structure) but lacking the catalytic core and ATP binding site critical for catalytic activity.

TRB-3 appears to represent one member of a family of kinase-like proteins without apparent catalytic activity; two cDNAs of unknown function, C5FW and C8FW, have also been identified in thyroid cells (Wilkin et al., *J. Biol. Chem.* 271:28451–28457, 1996; Wilkin et al., *Eur. J. Biochem.* 248:660–668, 1997) (see FIG. 1, SEQ ID NO:4 and 5, respectively). TRB shares extensive homology with these proteins, not only within conserved kinase subdomains VIb–XI, but also in sequences flanking these regions. In lower animals, TRB shares more limited sequence homology with Tribbles, a *Drosophila* protein that inhibits mitosis early in development by binding to the CDC25 homolog string (Mata et al., *Cell* 101:511–522, 2000; Rorth et al., *Mol. Cell.* 6:23–30, 2000; Seher and Leptin, *Curr. Biol.* 10:623–629, 2000). Tribbles blocks string activity by promoting its ubiquitination and proteasome mediated degradation.

EXAMPLE 2

TRB-3 Physically Interacts with PKB/Akt Kinases

Mammalian two hybrid assays in HEK293 cells using GAL4 Akt (ΔPH) (amino acids 150–480) and TRB-3 VP16 expression vectors confirmed the interaction between TRB-3 and Akt. Relative to a control VP16 expression vector, TRB-3-VP16 induced GAL4 Akt activity 5-fold on a co-transfected GAL4 luciferase reporter plasmid but had no effect on a GAL4 DNA binding domain (DBD) alone vector (see FIG. 2A).

GST pull down assays were done with baculovirus expressed GST-Akt. For co-immunoprecipitation of epitope-tagged proteins, cells were transfected with Akt fused to hemaglutinin antigen (2 μg) and Flag-TRB-3 (2 μg) expression vectors by Lipofectamine 2000 according to the manufacturer's instructions. Transfected cells were harvested and lysed in Co-IP buffer (25 mM Tris (pH 7.6), 150 mM NaCl, 2.5 mM $MgCl_2$, 0.5 mM EDTA, 0.5% NP-40, 5 mM β-glycerophosphate, 1 mM DTT, 5% glycerol, and proteinase inhibitors). Total cell lysate (500 μg) was subjected to immunoprecipitation with immobilized anti-HA monoclonal antibodies (COVANCE). For co-immunoprecipitation studies on endogenous Akt and TRB-3 proteins, total cell lysate from HepG2 cells was incubated with antiserum to TRB-3. Immunoprecipitates were separated by SDS-PAGE (12% gels), and proteins were analyzed by Western blot assay using monoclonal antiserum to Akt.

To further evaluate the interaction between Akt and TRB-3, affinity selection assays with GST-Akt or control GST plus $^{35}$S-labeled TRB-3 from rabbit reticulocyte lysate programmed with TRB-3 RNA were performed. TRB-3 was efficiently retained on GST-Akt but not control GST resin in pull-down assays (see FIG. 2B). Co-immunoprecipitation (CO-IP) studies on HEK293 cells transfected with Flag-tagged wild-type or mutant TRB-3 constructs plus HA-tagged Akt also confirmed the interaction between the two proteins. Wild-type TRB-3 was recovered from immunoprecipitates of HA-tagged Akt, confirming the ability of these proteins to interact with one another (see FIG. 2C).

To determine whether endogenous TRB-3 and Akt are associated in vivo, a polyclonal antiserum to the $NH_2$-terminal 145 amino acid residues of TRB-3 was generated, which are not conserved in TRB-1 or TRB-2. In Western blot assays of HepG2 hepatocyte extracts, antiserum to TRB-3 recognized a single band of 45 kDa, which is consistent with the predicted molecular size of the protein (see FIG. 2F). Immunoprecipitation of proteins from HepG2 whole-cell extracts with antiserum to TRB-3 revealed a 60 kDa band that interacted with antibody to Akt (see FIG. 2F). No Akt was detected in immunoprecipitates prepared with pre-immune serum (Pre) or with antiserum to TRB-3 that was blocked by incubation with recombinant TRB-3 peptide. Confirming the association noted with endogenous proteins, Flag-tagged TRB-3 was recovered from immunoprecipitates of HA-tagged Akt1 in transfected cells (see FIG. 2C). TRB-3 was also detected in immunoprecipitates of Akt2, suggesting a more general involvement of TRB-3 in regulating cellular Akt activity.

In the course of experiments to identify relevant interaction domains in TRB-3 and Akt, a putative TRB-3 alternative splice product from the EST database, which lacks 26 amino acids covering subdomain IX (residues 265–289; within the conserved kinase domain) of TRB-3 was also identified (see FIG. 2D). Compared with the wild-type protein, this ΔTRB-3 (Δ) polypeptide interacted more weakly with Akt in co-immunoprecipitation assays (see FIG. 2C), suggesting that this isoform of TRB-3 has distinct, perhaps opposing, biological activities to the full length protein. TRB-2 was also found to interact with over-expressed Akt in co-immunoprecipitation assays.

Immunofluorescence studies were performed to identify cellular locations in which TRB-3 is likely to interact with and to regulate Akt activity. Following transfection of CHO cells with an Akt-GFP (green fluorescent protein) chimera and Flag-tagged TRB-3 expression constructs, Akt-GFP fluorescence was detected primarily in the cytoplasmic compartment, coinciding with Flag-TRB-3 immunoreactivity (see FIG. 2E). Similar results were obtained in cells transfected with HA-Akt and TRB-3-GFP constructs, arguing against potential effects of FLAG and GFP tags on Akt or TRB-3 localization.

EXAMPLE 3

TRB-3 Modulates Phosphorylation and Activation of PKB/Akt Kinases

To determine whether TRB-3 modulates Akt activation in response to extracellular signals, Western blot assays using antibodies specific for a phosphorylated Akt were performed. Protein was extracted in SDS-Urea-lysis buffer, and 20 μg of protein were loaded onto a 12% SDS-polyacrylamide gel and blotted onto a nitrocellulose membrane. Western blot assays were performed as previously described (Michael et al., *Mol. Cell. Biol.* 20:1596–1603, 2000) using specific antibodies against the non-phosphorylated or phosphorylated forms of PKB/Akt or GSK3, respectively (Cell Signaling, Beverly, Mass.; Santa Cruz, Santa Cruz, Calif.). Anti-TRB-3 rabbit polyclonal antiserum was generated against GST-TRB-3 polypeptide (amino acids 1–145 of mouse TRB-3).

Western blots were performed with phospho Ser473 specific Akt antiserum on immunoprecipitates of HA-tagged Akt prepared from transfected HepG2 cells following stimulation with IGF, a potent inducer of Akt phosphorylation and activation. IGF treatment stimulated Akt phosphorylation and activation 3–4 fold after 15 minutes (see FIG. 3A). In titration experiments, over-expression of TRB-3 inhibited Akt phosphorylation in a dose-dependent manner but had no effect on total levels of Akt protein. Similarly, over-expression of TRB-3 blocked phosphorylation of Akt in COS7 cells in response to the phosphatase inhibitor pervanadate (see FIG. 3B), suggesting that TRB-3 either interferes with PDK-1 dependent phosphorylation of Akt (Thr308), with potential auto-phosphorylation by Akt at Ser473 itself, or promotes rapid dephosphorylation by Akt phosphatases such as PP2A.

Phosphorylation of Akt1 at Thr308 and Ser473 is tightly correlated with its activation. To determine whether the association with TRB-3 modulates Akt activity, Akt phosphorylation in response to growth factor stimuli was monitored. Treatment of HEK293 cells with insulin-like growth factor (IGF1) induced phosphorylation of Akt at $Thr^{308}$ and $Ser^{473}$ within 15 minutes. Expression of TRB-3 inhibited Akt phosphorylation at both sites without altering total amounts of Akt protein. TRB-2 was similarly effective at blocking Akt phosphorylation. Over-expression of TRB-3 reduced Akt activity, as determined by in vitro kinase assays with a peptide substrate corresponding to the consensus sequence recognized by Akt. The ΔTRB-3 polypeptide did not inhibit Akt kinase activity. Thus unlike tribbles, which inhibits CDC25 and C/EBP in *Drosophila* by triggering ubiquitin-mediated proteolysis of these proteins, TRB-3 appears to block Akt activity by disrupting its phosphorylation without reducing the abundance of the protein.

Akt has been shown to inhibit the activity of members of the forkhead family of transcriptional activators by directly phosphorylating residues that lead to nuclear export and complex formation with cytoplasmic 14-3-3 proteins. The co-localization of TRB-3 with Akt in the nucleus prompted examination of whether TRB-3 modulates inhibitory effects of Akt on forkhead dependent transcription. Towards that end, transient transfection assays on HepG2 cells were performed. Over-expression of Foxo1 induced a 3× IRS luciferase reporter containing 3 insulin response elements from the IGFBP1 promoter about 4–5 fold; and co-transfection of constitutively active myristylated Akt construct completely repressed Foxo1 activity relative to kinase inactive Akt (see FIG. 3D). Over-expression of wild-type TRB-3 potentiated reporter activity in cells expressing catalytically inactive Akt, but had no effect in cells expressing myristylated Akt. By contrast, Akt interaction defective TRB-3 (ΔTRB-3) alternative splice product had no effect on wild-type Akt activity, suggesting that TRB-3 potentiates cellular gene expression via Foxo by blocking phosphorylation of Akt in vivo (see FIG. 3D).

To determine whether endogenous TRB-3 and Akt undergo complex formation, polyclonal antiserum against TRB-3 were developed. TRB-3 was recovered from immunoprecipitates of phospho Ser473 Akt prepared from insulin treated but not control FAO cells, indicating that TRB-3 interacts with Akt in vivo.

Figure 4:
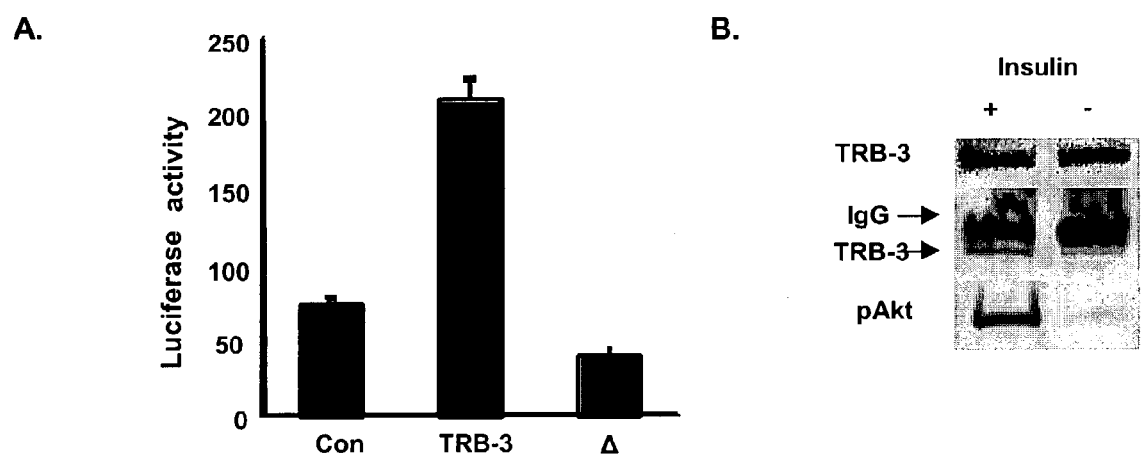
FIG. 4 collectively shows the effects of TRB-3 on Akt.

Following its activation in response to growth factor signals, Akt is known to regulate cellular gene expression in part via phosphorylation of forkhead (FKHR) family members. Phosphorylation of FKHR proteins, in turn, appears to inhibit target gene expression by promoting nuclear export of these proteins. To test whether TRB-3 modulates FKHR activity via its interaction with Akt, transient transfection assays in HEK293 cells transfected with Foxo1 effector plasmid plus an IGFBP1 reporter containing 3 forkhead binding sites were performed. Over-expression of TRB-3 potentiated forkhead activity 3-fold in HEK293 cells (see FIG. 4). By contrast, Akt interaction defective TRB-3 (ΔTRB-3) alternative splice product had no effect on IGFBP1 reporter activity, supporting the notion that TRB-3 potentiates cellular gene expression via Foxo1 by blocking phosphorylation of Akt (see FIG. 4).

The ability of TRB-3 to interfere with Akt activation in response to growth factor stimuli prompted evaluation of the role of this protein in insulin signaling. Towards that end, an adenovirus TRB-3 expression vector that co-expresses green fluorescent protein as a convenient marker of infection efficiency was developed. A TRB-3-expressing adenovirus was generated through homologous recombination between a linearized transfer vector pAD-Track and the adenoviral backbone vector pAD-Easy as described previously (He et al., *Proc. Natl. Acad. Sci. USA* 95:2509–2514, 1998). pAD-TRB-3 contained the full-length murine TRB-3 cDNA or variant ΔTRB-3 with an N-terminal Flag-tag. In addition to the TRB-3 transgene, the virus encoded the green fluorescent protein (GFP) transcribed from an second independent CMV promoter.

GFP expression was used to monitor viral infection efficiency. An adenovirus coding for GFP only (pAD-GFP) was used as a control in all experiments. Viruses were purified by the CsCl method and dialyzed against PBS buffer containing 10% glycerol as described previously (Becker et al., *Meth. Cell. Biol.* 43A:161–189, 1994). Using a polyclonal antiserum against TRB-3, an endogenous 50 kD TRB-3 immunoreactive band in FAO hepatoma cells that was strongly enhanced following infection with TRB-3 adenovirus was detected (see FIG. 5A, top).

To determine the effect of TRB-3 on insulin signaling in hepatocytes, a glucose output assay on mouse FAO hepatoma cells was employed. Cells were cultured in six-well plates in DMEM with 10% FBS and infected 48 hours after plating with adenoviruses expressing either GFP or TRB-3. 48 hours after infection, cells were treated with 10 μM forskolin and 10 μM dexamethasone overnight and, subsequently, treated with 30 nM insulin for 3 hours where indicated. The medium was then replaced with 2 ml of glucose production buffer comprising glucose-free DMEM, without phenol red, supplemented with 20 mM sodium lactate and 2 mM sodium pyruvate. After a 3 hour incubation, 0.4 ml of medium was assayed for glucose concentration using a colorimetric glucose assay kit (Sigma). Readings were normalized to the total protein content determined from the whole-cell lysate.

Figure 8:
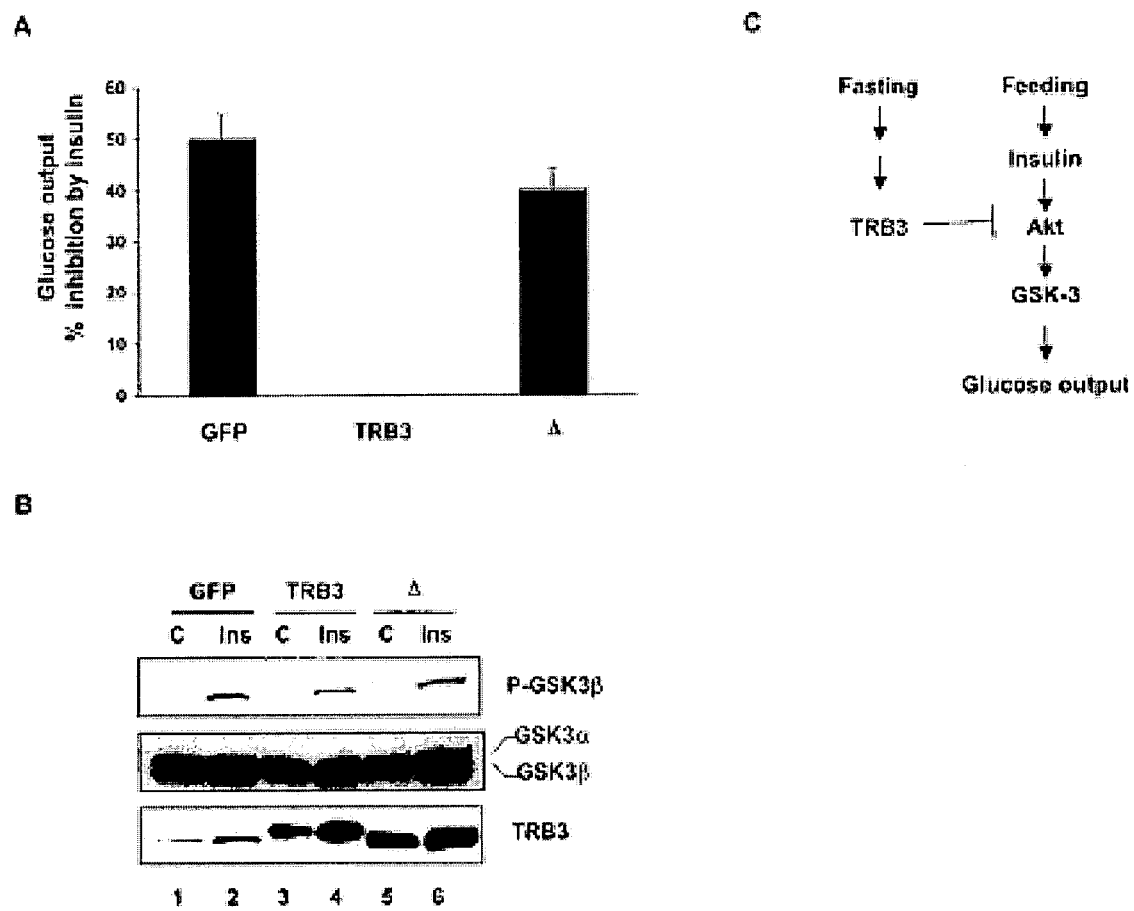
FIG. 8 collectively shows the blockade of insulin action by TRB-3 in cultured hepatocytes.

Glucose output from control FAO cells infected with GFP adenovirus construct was inhibited 3–4 fold by treatment with insulin at $10^{-7}$ M (see FIG. 5A, bottom); in a second experiment glucose output was inhibited 50% by treatment with insulin at $10^{-8}$ M (see FIG. 8A). Following infection with TRB-3 adenovirus, however, basal glucose output rose 5-fold and the inhibitory effect of insulin on glucose production was severely blunted (see FIG. 5A, bottom); in the second experiment the inhibitory effect of insulin on glucose output was almost completely blocked (see FIG. 8A). An adenovirus construct expressing the ΔTRB-3 polypeptide had no effect on insulin signaling. These results indicate that TRB-3 promotes signaling by counter-regulatory hormones (cAMP/dexamethasone) during the fasting period by blocking insulin effects.

To determine the mechanism by which TRB-3 promotes glucose production in FAO cells, the phosphorylation status of GSK-3β (an in vivo target for Akt) was examined. Consistent with its inhibitory effects on glycogenolysis, insulin stimulated Ser9 phosphorylation of GSK-3β in control FAO cells infected with control GFP adenovirus (see FIG. 5B, lanes 1 and 2). By contrast, phosphorylation of GSK-3β on Ser9 was severely reduced in cells infected with Adeno TRB-3, indicating that TRB-3 promotes glucose production at least in part by suppressing insulin effects on glycogen breakdown (see FIG. 5B, comparing lanes 2 and 5).

Should TRB-3 regulate Akt activity during the fasting period, then disrupting TRB-3 expression may enhance insulin-dependent suppression of gluconeogenic genes. For RNA interference (RNAi) experiments, double stranded RNA duplexes corresponding to amino acids 34–40 of rat and mouse (5'-CGAGUGAGAGAUGAGCCUG-3'; SEQ ID NO:13) or human (5'-CGAGCUCGAAGUGGGCCCC-3'; SEQ ID NO:14 TRB3 were purified, annealed, and transfected into human HepG2 hepatocytes. The effect of RNAi on TRB-3 expression and on insulin dependent Akt activation was measured after 24 to 48 hours. Mouse- and rat-specific TRB-3 duplex oligos were used as control oligos in experiments with human HepG2 cells. All RNAi experiments were performed on at least three independent occasions with comparable results.

Human hepatoma HepG2 cells were cultured in modified Eagle's medium (MEM) (4.5 glucose/liter) supplemented with 10% fetal bovine serum, MEM-non essential amino acids, sodium pyruvate, 100 U of penicillin/ml, and 100 μg of streptomycin/ml. HepG2 cells were plated in a 24-well cell culture dish and transfected using the Lipofectamine 2000 reagent (GIBCO BRL) according to manufacturer's instructions (500 ng of indicator plasmid/well). Duplexed small interfering RNA oligos (siRNA) directed against human TRB-3 were co-transfected as described previously (Elbashir et al., *Nature* 411:494–498, 2001). Control experiments contained nonspecific siRNA oligos. Groups of cells were serum starved for 10 hours and, subsequently, treated with forskolin (10 μM final concentration), dexamethasone (10 μM final concentration), and/or insulin (30 nM final concentration) overnight. Cell extracts were prepared 48 hours after transfection and a luciferase assay was performed as described previously (Nakajima et al., *Cell* 90:1107–1112, 1997). Reporter activities were normalized to activity from cotransfected Rous sarcoma virus-beta-galactosidase expression plasmid.

Figure 5:
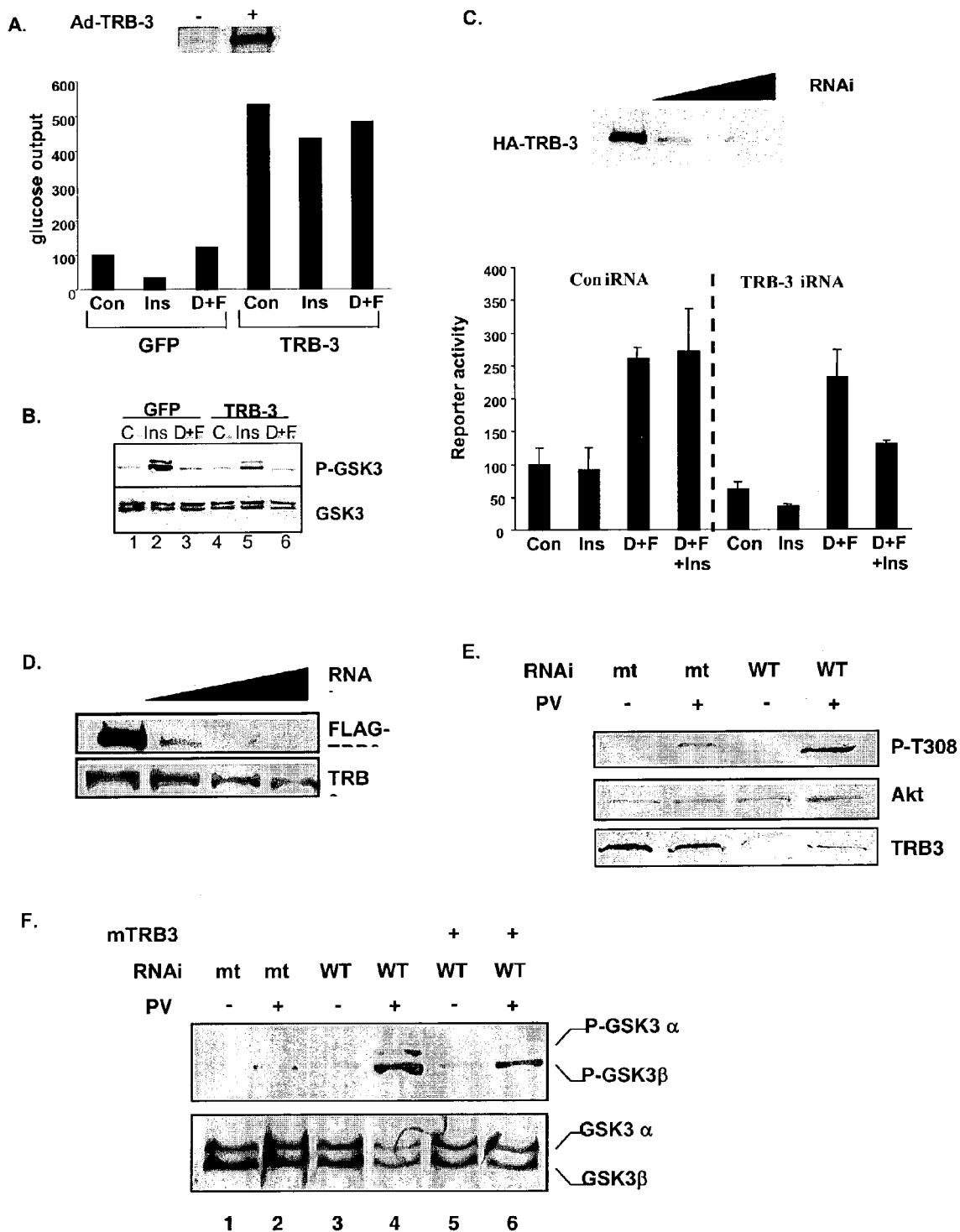
FIG. 5 collectively shows additional effects of TRB-3 on Akt.

In control experiments on HepG2 cells transfected with HA tagged TRB-3 expression vector, TRB-3 RNAi efficiently disrupted expression of TRB-3 protein relative to control mutant oligos, by Western blot assay (see FIG. 5C, top). Treatment with forskolin and dexamethasone stimulated a PEPCK reporter plasmid 2.5 fold in HepG2 hepatocytes. Consistent with previous reports (Yeagley et al., *J. Biol. Chem.* 275:17814–17820, 2000), insulin treatment had little effect on PEPCK promoter activity, either alone or in combination with forskolin plus dexamethasone (see FIG. 5C, bottom). Following co-transfection with wild-type TRB-3 RNAi oligos, however, insulin was found to inhibit PEPCK promoter activity 2-fold in response to insulin (see FIG. 5C, bottom). As mutant RNAi oligos showed no effect in this regard, these experiments indicate that TRB-3 promotes hepatic gluconeogenesis under fasting conditions by blocking Akt-mediated inhibition of gluconeogenic gene expression.

To determine whether the inhibitory action of TRB-3 on Akt is physiologically relevant, endogenous TRB3 expression was disrupted in hepatocytes by RNA interference (RNAi). In transient transfection assays, a 21 bp TRB-3 RNA duplex oligonucleotide reduced the abundance of both endogenous TRB-3 and over-expressed Flag-TRB3-protein in a dosage-dependent manner (see FIGS. 3F and 5D). RNAi mediated knockdown of TRB-3 in HepG2 cells potentiated Akt phosphorylation at Thr308 and Ser473 in response to growth factor signaling (see FIGS. 3F and 5E). Correspondingly, disruption of TRB-3 expression also enhanced phosphorylation of Akt substrates such as GSK3β (Ser9) and Foxo (Ser256) in response to insulin and pervanadate, a potent activator of Akt. The effects of TRB-3 RNAi appeared to be specific as co-transfection of a mouse TRB-3 expression vector, not recognized by the human TRB-3 RNAi oligo used in this study, reversed this phenotype (see FIG. 5F).

To determine the mechanism by which TRB-3 may inhibit Akt activity, mammalian two-hybrid assays using TRB-3-VP16 expression plasmid and mutant GAL4 Akt constructs were performed. Relative to the wild-type protein, phosphorylation defective T308A mutant Akt appeared to associate more efficiently with TRB-3 (see FIG. 3G). By contrast, substitution of Thr308 with Asp to mimic Thr308 phosphorylation strongly inhibited the interaction between TRB-3 and Akt (see FIG. 3G), suggesting that TRB-3 preferentially binds to the unphosphorylated form of the kinase. Indeed, assays with a series of truncated Akt expression vectors revealed that amino acid residues 240–315 in Akt1 are essential for this association, indicating that TRB-3 may block Akt activation by binding directly to and masking the Thr308 phosphorylation site (see FIG. 3G). Consistent with results from co-immunoprecipitation studies, a GAL4 Akt2 construct interacted with TRB-3 comparably to Akt1, suggesting that TRB-3 may perform a general role in regulating cellular Akt activity.

To perform in vitro kinase assays, human embryonic kidney cells (HEK 293) were co-transfected with an expression vector encoding HA-Akt and either a vector encoding TRB3 or empty expression vector. One day after transfection, cells were deprived of serum for 16 hours and then treated with 100 μM of sodium pervanadate or vehicle for 15 minutes. Cells were lysed in lysis buffer (20 mM Tris (pH 7.6), 150 nm NaCl, 1 mM EDTA, 1 mM EGTA, 1% Triton X-100, 2.5 mM β-Glycerophosphate, 1 mM sodium pervanadate and proteinase inhibitors), and HA-tagged Akt was immunoprecipitated with monoclonal antibody to HA. Immune complexes were washed, and in vitro kinase assays were performed with recombinant GST-GSRSRRPSYRL polypeptide (SEQ ID NO:15; 2 μg per reaction) as substrate. Reactions were incubated in kinase assay buffer (20 mM Tris pH 7.6, 5 mM β-glycerophosphate, 2 mM DTT, 0.1 mM sodium pervanadate, 10 mM $MgCl_2$, 200 μM cold ATP, 1 μCi [γ-$p^{32}$]-ATP) at 30 degrees C. for 30 minutes. Reactions were terminated by addition of 2× SDS-PAGE loading buffer, and phosphorylated substrate was resolved by SDS-PAGE (12% gels). Radio-labeled bands were quantified by phosphoimager.

EXAMPLE 4

TRB-3 Expression is Induced Under Fasting and Diabetic States and Promotes Insulin Resistance The ability of TRB-3 to block insulin dependent signaling in isolated hepatocytes prompted examination of the dynamics of TRB-3 expression in liver under fasting or feeding conditions.

Male 6-week old C57Bl6 mice were obtained from Harlan (San Diego, Calif.) and housed in an air-conditioned environment, with a 12 hour light-dark cycle, and were fed a regular unrestricted diet. Animals were anaesthetized with Iso-Flurane and a total of $1 \times 10^9$ plaque-forming units per recombinant virus was administered via systemic tail vein injection. In each experiment at least 7 animals received identical treatments. During the course of the experiments animals were fasted for 24 hours overnight with free access to water and fasting blood glucose was monitored after this period. Mice were then refed for the following 24 hours and fed blood glucose was determined thereafter. This fasting-feeding protocol was maintained for at least 7 consecutive days. All mice were sacrificed for blood and tissue collection at the end of the experiment. Blood samples were collected from the tail vein. Plasma was obtained by centrifugation of collected blood and assayed for insulin. Liver tissue for RNA and protein isolation was immediately frozen in liquid nitrogen and stored at −80° C. Cryomicrotome sections of liver samples were used to assess viral infection efficiency by fluorescence microscopy.

For glucose tolerance tests, mice were fasted for 24 hours overnight and, subsequently, injected with 1 unit glucose per gram body weight into the peritoneal cavity. Glucose levels were measured from blood collected from the tail immediately before and 10, 20, 30, 60, and 120 minutes after the injection. Blood glucose values were determined from whole blood using an automatic glucose monitor (One Touch Ultra, Lifescan). Plasma insulin levels were determined using a commercial insulin ELISA kit (Crystal Chem. Inc., Chicago). Hepatic glycogen content was also determines as milligrams per gram wet liver tissue. All procedures were performed according to the directions provided by the manufacturers.

Total RNA was extracted from homogenized mice livers and FAO liver cells using the RNeasy (Qiagen, Valencia) kit including DNase I treatment. RNA quality was assessed by gel electrophoresis. cDNA was prepared by reverse transcription of 750 ng total RNA using the Superscript II enzyme and Oligo dT primer (GIBCO BRL, Grand Island). The resulting cDNAs were amplified using the SYBR green PCR kit and a ABIPRISM 7700 Sequence detector (Perkin Elmer, Foster City). The PCR reactions were conducted as follows: 10 minutes at 95° C. (initial polymerase activation), 30 seconds at 95° C., 30 seconds at 60° C., 45 seconds at 72° C., for 40 cycles. All RNA expression data from the TaqMan analysis were calculated using the standard curve method (Perkin Elmer) and normalized to the expression of the ribosomal 36B4 gene in the corresponding sample. Specific primer pairs were directed against murine genes for PEPCK, glucose-6-phosphatase, glucokinase, and pyruvate dehydrogenase kinase 4. The presence of only one specific PCR product was verified for each primer pair by agarose gel electrophoresis of the SYBR green reaction mixture.

Figure 6:
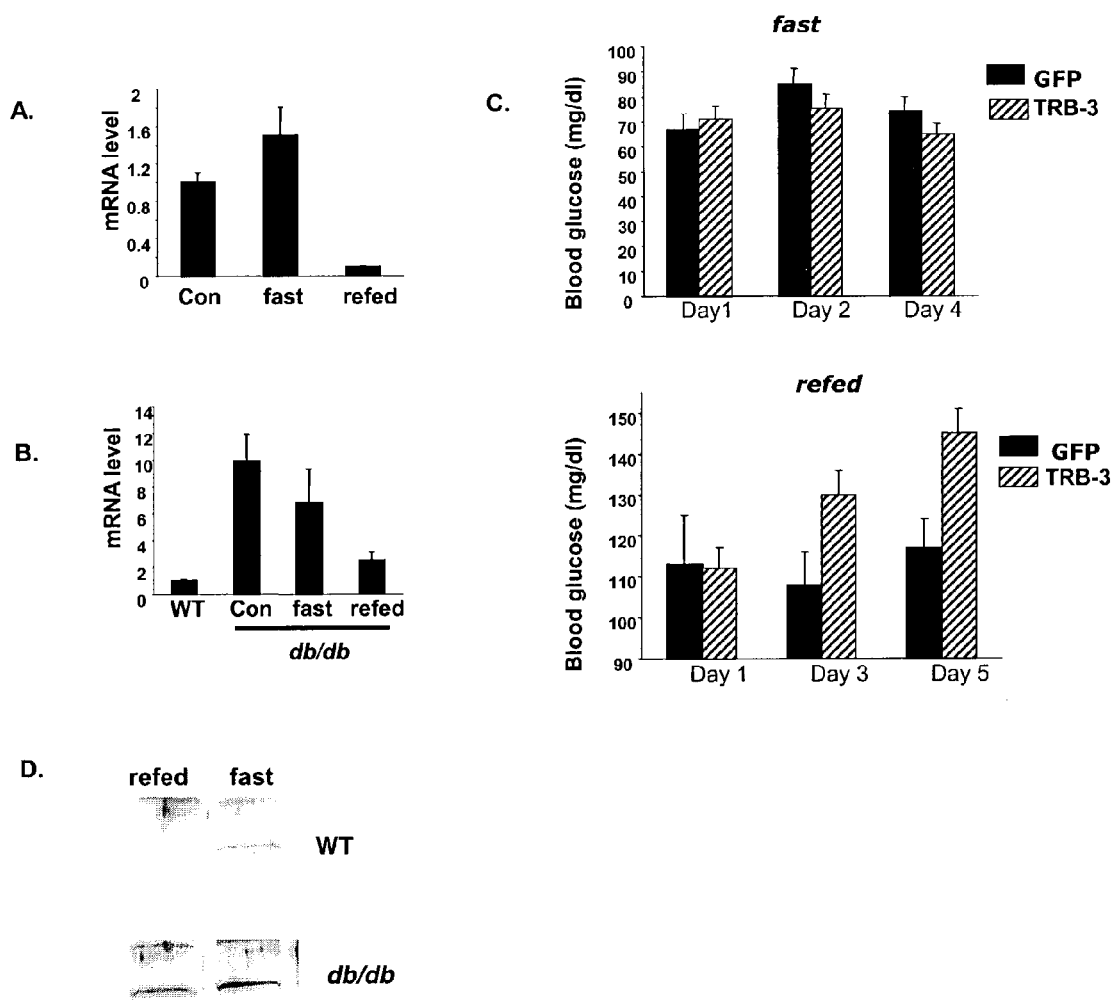
FIG. 6 collectively shows that TRB-3 promotes insulin resistance in vivo.

In these quantitative PCR assays, hepatic TRB-3 RNA levels were induced 10–20 fold under fasting conditions compared to the fed state (see FIG. 6A, top and FIG. 6D). Remarkably, TRB-3 RNA levels were further induced 10-fold in db/db diabetic mice compared to wild-type mice under feeding conditions, and showed only marginal changes in TRB-3 expression during the fasting to feeding transition (see FIG. 6A, bottom and FIG. 6D). Amounts of TRB-1 and TRB-2 did not vary with nutritional status. Supporting a role for counter-regulatory hormones in stimulating TRB-3 expression under fasting conditions, levels of TRB-3 RNA were induced 2–3 fold in FAO hepatocytes following treatment with either glucocorticoids or cAMP agonist (see FIG. 9A). Taken together, these results suggest that TRB-3 could inhibit Akt specifically during fasting, and that inappropriate expression of TRB-3 in diabetes may contribute to insulin resistance by blocking Akt activity in the fed state. Indeed, Akt was readily detected in immuno- precipitates of TRB-3 prepared from whole liver extracts from fasted db/db mice, demonstrating that the TRB-3:Akt complex is present in liver under fasting conditions (see FIG. 9B).

Figure 7:
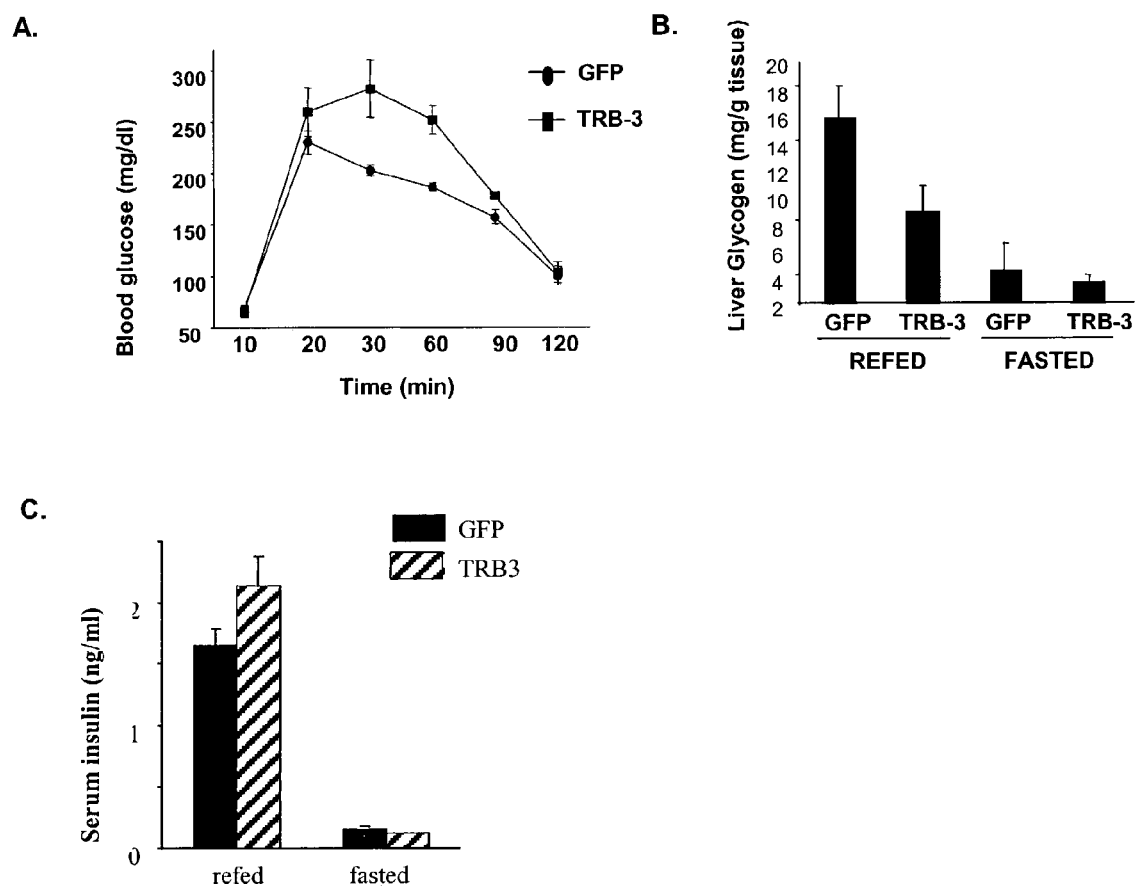
FIG. 7 collectively shows various levels in TRB-3 adenovirus infected mice.

To test the role of TRB-3 in glucose homeostasis in vivo, adult male C57B16 mice (n=7 per group) were infected with TRB-3 or control GFP adenoviruses and blood glucose levels under fasting and refed conditions were monitored. In animals infected with TRB-3 adenovirus, amounts of TRB-3 RNA and protein in liver were 1.5 to 2 fold higher than those observed in db/db diabetic mice (see FIG. 9C). Over-expression of TRB-3 had no effect on blood glucose production under fasting conditions compared to control mice infected with control adenovirus (see FIG. 6B). By contrast, blood glucose levels were significantly elevated in the refed state 5 days after infection (150 mg/dl vs. 115; n=7), indicating that TRB-3 interferes with acute effects of insulin on hepatic glucose release (see FIG. 6B, bottom). Consistent with the notion that TRB-3 contributes to insulin resistance, plasma insulin concentrations in the refed state were modestly increased in TRB-3 infected (2.2 ng/ml) versus GFP control (1.6 ng/ml) mice (see FIG. 7C). In this regard, TRB-3 Adenovirus infected mice showed impaired glucose tolerance; following intraperitoneal glucose injection (2 g/kg), blood glucose levels in TRB-3 infected mice remained significantly higher than in control mice (see FIG. 7A). Remarkably, liver glycogen content in TRB-3 adenovirus infected mice was 2-fold lower in the fed state (8 mg/g tissue vs. 16 mg/g tissue; n=4) indicating that much of the hyperglycemic effects of TRB-3 is due to elevated hepatic glycogenolysis and/or reduced synthesis (see FIG. 7B).

Under physiologic conditions, insulin inhibits glycogenolysis by promoting the Akt-dependent phosphorylation of GSK-3β at Ser9. The dual importance of GSK-3 as a regulator of glucose production and as a bona fide substrate of Akt prompted examination of whether TRB-3 mediated inhibition of Akt correspondingly reduced insulin-dependent phosphorylation of GSK-3. Compared with hepatocytes infected with control GFP adenovirus, cells infected with wild-type TRB-3 adenovirus showed reduced insulin dependent phosphorylation of GSK-3β on Ser9 (see FIG. 8B). But mutant ΔTRB-3 adenovirus had no effect in this regard, indicating that TRB-3 interferes with insulin effects on glucose output, at least in part, by blocking phosphorylation of relevant Akt substrates.

Taken together, our results suggest that TRB-3 promotes glucose output from liver under fasting conditions by binding to and interfering with Akt phosphorylation in response to residual insulin signaling (see FIG. 8C). Pathologic over-expression of TRB-3 in the fed state may therefore contribute to insulin resistance and promote hyperglycemia. These results also provide a molecular explanation for the insulin resistance which has been observed under chronic fasting conditions and in response to counter-regulatory hormones like dexamethasone. In this regard, prolonged starvation has been shown to blunt the stimulatory effect of insulin on glycogen synthase activity. Moreover, glucocorticoids have been found to promote insulin resistance in adipocytes, in part, by reducing insulin-stimulated Akt activation. The observed expression of TRB-3 in response to diabetes and fasting may explain these findings and establish TRB-3 as an attractive drug target in the treatment of type II diabetes.

While the invention has been described and exemplified in sufficient detail for those skilled in this art to make and use it, various alternatives, modifications, and improvements should be apparent without departing from the spirit and scope of the invention. The present invention is well adapted to carry out the objects and obtain the ends and advantages mentioned, as well as those inherent therein. The examples provided here are representative of preferred embodiments, are exemplary, and are not intended as limitations on the scope of the invention. Modifications therein and other uses will occur to those skilled in the art. These modifications are encompassed within the spirit of the invention and are defined by the scope of the claims.

The disclosure of all publications cited above are expressly incorporated herein by reference, each in its entirety, to the same extent as if each were incorporated by reference individually.

The invention claimed is:

1. A method for screening test compounds to determine if any disrupt the interaction between an inhibitor of protein kinase B (PKB)/Akt protein and a PKB/Akt protein, said method comprising:

assaying for complex formation between said inhibitor and said PKB/Akt protein in the presence and absence of a test compound, wherein said inhibitor of PKB/Akt protein is a Tribbles (TRB) family protein selected from the group consisting of human TRB-3 having the sequence set forth in SEQ ID NO:1, mouse TRB-3 having the sequence set forth in SEQ ID NO:2, rat TRB-3 having the sequence set forth in SEQ ID NO:3, C5FW having the sequence set forth in SEQ ID NO:4, C8FW having the sequence set forth in SEQ ID NO:5, Drosophila Tribbles protein having the sequence set forth in SEQ ID NO:6, TRB-1 having the sequence set forth in SEQ ID NO:7, and TRB-2 having the sequence set forth in SEQ ID NO:8; and wherein a decrease in the level of complex formation in the presence of said test compound, relative to complex formation in the absence of said test compound, is indicative of a compound that disrupts said interaction.

2. A method according to claim 1, wherein said inhibitor of PKB/Akt protein is a Tribbles (TRB) family protein selected from the group consisting of human TRB-3 having the sequence set forth in SEQ ID NO:1, mouse TRB-3 having the sequence set forth in SEQ ID NO:2, rat TRB-3 having the sequence set forth in SEQ ID NO:3, C5FW having the sequence set forth in SEQ ID NO:4, C8FW having the sequence set forth in SEQ ID NO:5, TRB-1 having the sequence set forth in SEQ ID NO:7, and TRB-2 having the sequence set forth in SEQ ID NO:8.

3. A method according to claim 2, wherein said TRB family protein is selected from the group consisting of human TRB-3 having the sequence set forth in SEQ ID NO:1, mouse TRB-3 having the sequence set forth in SEQ ID NO:2, and rat TRB-3 having the sequence set forth in SEQ ID NO:3.

4. A method according to claim 2, wherein said TRB family protein is selected from the group consisting of C5FW having the sequence set forth in SEQ ID NO:4, C8FW having the sequence set forth in SEQ ID NO:5, TRB-1 having the sequence set forth in SEQ ID NO:7, and TRB-2 having the sequence set forth in SEQ ID NO:8.

5. A method for identifying a compound that disrupts the interaction between an inhibitor of PKB/Akt protein and a PKB/Akt protein, said method comprising:

contacting said inhibitor and said PKB/Akt protein in the presence and absence of a test compound, and determining whether said test compound decreases the level of complex formation between said inhibitor and said PKB/Akt protein, relative to the level of complex formation in the absence of said test compound, thereby identifying a compound that disrupts said interaction:

wherein said inhibitor of PKB/Akt protein is a Tribbles (TRB) family protein selected from the group consisting of human TRB-3 having the sequence set forth in SEQ ID NO:1, mouse TRB-3 having the sequence set forth in SEQ ID NO:2, rat TRB-3 having the sequence set forth in SEQ ID NO:3, C5FW having the sequence set forth in SEQ ID NO:4, C8FW having the sequence set forth in SEQ ID NO:5, Drosophila Tribbles protein having the sequence set forth in SEQ ID NO:6, TRB-1 having the sequence set forth in SEQ ID NO:7, and TRB-2 having the sequence set forth in SEQ ID NO:8.

6. A method for screening test compounds to determine if any affect the phosphorylation state of a mammalian protein kinase B (PKB)/Akt protein kinase, said method comprising:

assaying for the phosphorylation level of said PKB/Akt protein in the presence of an inhibitor of PKB/Akt protein and a test compound relative to the phosphorylation level of said PKB/Akt protein in the presence of said modulator alone;

wherein said inhibitor of PKB/Akt protein is a Tribbles (TRB) family protein selected from the group consisting of human TRB-3 having the sequence set forth in SEQ ID NO:1, mouse TRB-3 having the sequence set forth in SEQ ID NO:2, rat TRB-3 having the sequence set forth in SEQ ID NO:3, C5FW having the sequence set forth in SEQ ID NO:4, C8FW having the sequence set forth in SEQ ID NO:5, Drosophila Tribbles protein having the sequence set forth in SEQ ID NO:6, TRB-1 having the sequence set forth in SEQ ID NO:7, and TRB-2 having the sequence set forth in SEQ ID NO:8; and wherein a change in said phosphorylation level is indicative of a compound which affects the phosphorylation state of said PKB/Akt protein.

7. A method according to claim 6, wherein said TRB family protein is selected from the group consisting of human TRB-3 having the sequence set forth in SEQ ID NO:1, mouse TRB-3 having the sequence set forth in SEQ ID NO:2, and rat TRB-3 having the sequence set forth in SEQ ID NO:3.

8. A method according to claim 6, wherein said TRB family protein is selected from the group consisting of C5FW having the sequence set forth in SEQ ID NO:4, C8FW having the sequence set forth in SEQ ID NO:5, TRB-1 having the sequence set forth in SEQ ID NO:7, and TRB-2 having the sequence set forth in SEQ ID NO:8.

9. A method according to claim 6, wherein said TRB family protein is C5FW having the sequence set forth in SEQ ID NO:4.

10. A method according to claim 6, wherein said TRB family protein is C8FW having the sequence set forth in SEQ ID NO:5.

11. A method according to claim 6, wherein said TRB family protein is TRB-1 having the sequence set forth in SEQ ID NO:7.

12. A method according to claim 6, wherein said TRB family protein is TRB-2 having the sequence set forth in SEQ ID NO:8.

13. A method according to claim 6, wherein said TRB family protein is human TRB-3 having the sequence set forth in SEQ ID NO:1.

14. A method according to claim 6, wherein said TRB family protein is mouse TRB-3 having the sequence set forth in SEQ ID NO:2.

15. A method according to claim 6, wherein said TRB family protein is rat TRB-3 having the sequence set forth in SEQ ID NO:3.

* * * * *